(12) United States Patent
Fertig et al.

(10) Patent No.: US 7,396,944 B2
(45) Date of Patent: Jul. 8, 2008

(54) THIOPHENE DERIVATIVES, THEIR MANUFACTURE AND USE AS PHARMACEUTICAL AGENTS

(75) Inventors: Georg Fertig, Penzberg (DE); Frank Herting, Sindelsdorf (DE); Matthias Koerner, Antdorf (DE); Manfred Kubbies, Penzberg (DE); Anja Limberg, Penzberg (DE); Ulrike Reiff, Penzberg (DE); Ulrich Tibes, Starnberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 27 days.

(21) Appl. No.: 11/628,771

(22) PCT Filed: Jun. 13, 2005

(86) PCT No.: PCT/EP2005/006292

§ 371 (c)(1),
(2), (4) Date: Dec. 5, 2006

(87) PCT Pub. No.: WO2005/121134

PCT Pub. Date: Dec. 22, 2005

(65) Prior Publication Data

US 2007/0232602 A1     Oct. 4, 2007

(30) Foreign Application Priority Data

Jun. 14, 2004   (EP)   ................................. 04013861

(51) Int. Cl.
*C07D 333/10* (2006.01)

(52) U.S. Cl. ........................... 549/72; 549/59; 548/249; 548/365.7; 546/213; 546/280.4; 544/146; 544/379

(58) Field of Classification Search .................... 549/72, 549/59; 548/249, 365.7; 546/213, 280.4; 544/146, 379
See application file for complete search history.

(56) References Cited

U.S. PATENT DOCUMENTS

| 6,541,661 | B1 | 4/2003 | Delorme et al. |
| 6,784,173 | B2 | 8/2004 | Leser-Reiff et al. |
| 7,098,241 | B2 * | 8/2006 | Grossmann et al. ......... 514/448 |

FOREIGN PATENT DOCUMENTS

| WO | WO 01/38322 | 5/2001 |
| WO | WO 03/011851 | 2/2003 |
| WO | WO 03/076395 | 9/2003 |
| WO | WO 03/076430 | 9/2003 |
| WO | WO 03/076438 | 9/2003 |
| WO | WO 03/087066 | 10/2003 |

* cited by examiner

*Primary Examiner*—Bernard Dentz
*Assistant Examiner*—David E Gallis
(74) *Attorney, Agent, or Firm*—George W. Johnston; Patricia S. Rocha-Tramaloni; Gene J. Yao

(57) ABSTRACT

Objects of the present invention are the compounds of formula (I), their pharmaceutically acceptable salts, enantiomeric forms, diastereoisomers and racemates, the preparation of the above-mentioned compounds, medicaments containing them and their manufacture, as well as the use of the above-mentioned compounds in the control or prevention of illnesses such as cancer.

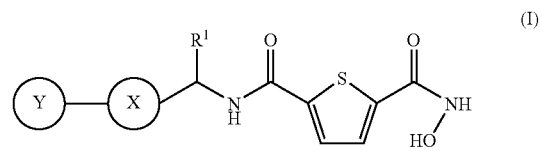

19 Claims, No Drawings

US 7,396,944 B2

THIOPHENE DERIVATIVES, THEIR MANUFACTURE AND USE AS PHARMACEUTICAL AGENTS

This application is the National Stage of International Application No. PCT/EP2005/006292, filed Jun. 13, 2005, which claims the benefit of European Application No. 04013861.2, filed Jun. 14, 2004, which is hereby incorporated by reference in its entirety.

The present invention relates to novel thiophene derivatives and to their (R)- and (S)-enantiomers and racemates, to a process for their manufacture, medicaments containing them and their manufacture as well as the use of these compounds as pharmaceutically active agents.

Transcriptional regulation is a major event in cell differentiation, proliferation, and apoptosis. Transcriptional activation of a set of genes determines cell destination and for this reason transcription is tightly regulated by a variety of factors. One of its regulatory mechanisms involved in the process is an alteration in the tertiary structure of DNA, which affects transcription by modulating the accessibility of transcription factors to their target DNA segments. Nucleosomal integrity is regulated by the acetylation status of the core histones. In a hypoacetylated state, nucleosomes are tightly compacted and thus are nonpermissive for transcription. On the other hand, nucleosomes are relaxed by acetylation of the core histones, with the result being permissiveness to transcription. The acetylation status of the histones is governed by the balance of the activities of histone acetyl transferase (HAT) and histone deacetylase (HDAC). Recently, HDAC inhibitors have been found to arrest growth and apoptosis in several types of cancer cells, including colon cancer, T-cell lymphoma, and erythroleukemic cells. Given that apoptosis is a crucial factor for cancer progression, HDAC inhibitors are promising reagents for cancer therapy as effective inducers of apoptosis (Koyama, Y., et al., Blood 96 (2000) 1490-1495).

Several structural classes of HDAC inhibitors have been identified and are reviewed in Marks, P. A., et al., J. Nat. Cancer Inst. 92 (2000) 1210-1216. More specifically, WO 98/55449, U.S. Pat. No. 5,369,108, WO 01/38322, WO 01/70675, WO 02/22577, WO 03/011851, WO 03/066579, WO 03/075929, WO 03/076395, WO 03/076400, WO 03/076401, WO 03/076421, WO 03/076422, WO 03/076430, WO 03/076438, WO 03/087066 and WO 2004/013130 report alkanoyl, alkylenyl, alkenylenyl, aryl, heteroaryl, benzyl, biaryl and cinnamyl hydroxamates with HDAC inhibitory activity.

However there remains a need for new compounds with improved therapeutic properties, such as enhanced activity, decreased toxicity, better solubility and improved pharmacokinetic profile, to name only a few.

The present invention relates to thiophene derivatives and to their (R)- and (S)-enantiomers and racemates according to formula I

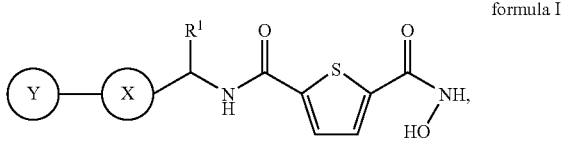

wherein
R[1] is alkyl, which is optionally substituted one or several times by halogen;

X is phenylene or heteroarylene;
Y is a saturated carbocyclic group;
a saturated heterocyclic group;
a heteroaryl group; or
a substituted phenyl group,
and all pharmaceutically acceptable salts thereof.

The compounds according to this invention are inhibitors of histone deacetylase (HDAC) and therefore possess antiproliferative activity. Objects of the present invention are the compounds of formula I and their pharmaceutically acceptable salts, diastereoisomers, racemates and especially their enantiomeric forms, the preparation of the compounds, medicaments containing such compounds and the manufacture of such medicaments as well as the use of such compounds in the control or prevention of illnesses, especially of illnesses and disorders as mentioned below or in the manufacture of corresponding medicaments.

Examples of tumors which may be treated with such compounds or medicaments, are colon cancers, breast carcinoma (including advanced breast cancer), lung cancer (e.g. adenocarcinoma and including non-small cell lung cancer), prostate cancer including advanced disease, pancreatic cancers, hematopoetic tumors of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MSD), tumors of mesenchymal origin, melanomas, teratocarcinomas, neuroblastomas, gliomas, benign tumors of the skin (e.g. keratoacanthomas), kidney carcinoma, ovary carcinoma, bladder carcinoma and epidermal carcinoma.

As used herein, the term "alkyl" means a saturated, straight-chain or branched-chain hydrocarbon containing from 1 to 6, preferably from 1 to 3, carbon atoms, such as methyl, ethyl, n-propyl, isopropyl, n-butyl, 2-butyl, t-butyl.

If said alkyl group is optionally substituted with one or several halogen atoms, it is preferably substituted with chlorine and fluorine, especially fluorine. Examples are difluoromethyl, trifluoromethyl, 2,2,2-trifluoroethyl, perfluoroethyl and the like.

The term "halogen" as used herein denotes fluorine, chlorine and bromine, preferably fluorine and chlorine.

The term "heteroarlyene" means a mono- or bicyclic aromatic ring with 5 to 10 ring atoms, which contains up to 3, preferably 1 or 2 heteroatoms selected independently from N, O or S and the remaining ring atoms being carbon atoms. Such heteroarylenes may be optionally substituted one or two times by alkyl which is defined as above, preferably by methyl. Examples of such heteroarylenes are thiophenediyl, isoxazolediyl, pyrrolediyl, methylthiophenediyl, furandiyl, imidazolediyl, pyridinediyl, pyrimidinediyl, pyrazinediyl, pyridazinediyl, triazinediyl, pyrazolediyl, oxazolediyl, methylisoxazolediyl, thiazolediyl, isothiazolediyl, thiadiazolediyl, oxadiazoldiyl, triazoldiyl, benzothiophenediyl, indolediyl, quinolinediyl, isoquinolinediyl, benzofurandiyl and the like, preferably thiophenediyl, isoxazolediyl, pyrrolediyl, especially thiophenediyl, or especially isoxazolediyl.

The term "saturated carbocyclic group" means a monocyclic saturated hydrocarbon ring with 3 to 7 ring atoms. Such saturated carbocyclic groups may be optionally substituted one or two times by alkyl which is defined as above, preferably by methyl. Examples of such saturated carbocyclic groups are cyclopropyl, cyclobutyl, and cycloheptyl, preferably cyclopentyl or cyclohexyl, especially cyclohexyl.

The term "saturated heterocyclic group" means a saturated, monocyclic hydrocarbon ring with 5 to 6 ring atoms which contains up to 3, preferably 1 or 2 heteroatoms selected independently from N, O or S and the remaining ring atoms being carbon atoms. Such saturated heterocyclic group can be optionally substituted one to three, preferably one or two times by alkyl, which is defined as above, preferably by methyl. Examples of such saturated heterocyclic groups are pyrrolidinyl, morpholino, piperazinyl, N-methyl-piperazinyl or piperidyl, especially morpholino, N-methyl-piperazinyl or piperidyl.

The term "heteroaryl group" means a mono- or bicyclic aromatic ring with 5 to 10 ring atoms, which contains up to 3, preferably 1 or 2 heteroatoms selected independently from N, O or S and the remaining ring atoms being carbon atoms. Such heteroaryl groups may be optionally substituted one or two times by halogen, —CN, —C(O)OH, —C(O)CH$_3$, —S—CH$_3$, —NH$_2$, —CH$_2$NH$_2$, —CH$_2$OH or alkyl, preferably by alkyl, wherein alkyl and halogen are defined as above. Examples of such heteroaryl groups are thiophenyl, methylthiophenyl, pyrazolyl, dimethylisoxazolyl, pyridyl, benzothiophenyl, indolyl, furyl, pyrrolyl, imidazolyl, pyrimidyl, pyrazinyl, pyridazinyl, triazinyl, oxazolyl, isoxazolyl, thiazolyl, isothiazolyl, thiadiazolyl, oxadiazolyl, triazolyl, quinolyl, isoquinolyl, benzofuranyl and the like, preferably thiophenyl, methylthiophenyl, pyrazolyl, dimethylisoxazolyl, pyridyl, benzothiophenyl or indolyl.

The term "substituted phenyl group" means a phenyl which is substituted one to three times by alkyl, halogen, —O-alkyl, —S(O)$_2$-alkyl, —NH(alkyl) or —N(alkyl)$_2$; wherein alkyl and halogen are defined as above and the alkyl groups may be optionally substituted with one or several halogen atoms, preferably with chlorine and fluorine, especially fluorine.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e., a drug) into a salt is a technique well known to pharmaceutical chemists to obtain improved physical and chemical stability, hygroscopicity, flowability and solubility of compounds. See, e.g., Stahl, P. H., and Wermuth, G., (editors), Handbook of Pharmaceutical Salts, Verlag Helvetica Chimica Acta (VHCA), Zürich (2002), or Bastin, R. J., et al., Organic Proc. Res. Dev. 4 (2000) 427-435.

In the compounds of formula I, R$^1$ is preferably methyl, ethyl or trifluoromethyl, especially methyl.

A further embodiment are compounds of formula I wherein X is phenylene or thiophenediyl.

A further embodiment are compounds of formula I wherein X is phenylene, thiophenediyl or isoxazolediyl.

A further embodiment are compounds of formula I wherein Y is a substituted phenyl group or heteroaryl group.

An embodiment of the invention are the (R)- or (S)-enantiomers or racemates of the compounds of formula I, wherein
Y is a substituted phenyl group.

Another preferred embodiment of the invention are the (R)- or (S)-enantiomers or racemates of the compounds of formula I, wherein
X is isoxazolediyl.

Another embodiment of the invention are the (R)- or (S)-enantiomers or racemates of the compounds of formula I, wherein
X is isoxazolediyl; and
Y is a substituted phenyl group.

Such compounds are for example:
Thiophene-2,5-dicarboxylic acid 2-hydroxyamide 5-({1-[5-(3-trifluoromethyl-phenyl)-isoxazol-3-yl]-ethyl}-amide); and
Thiophene-2,5-dicarboxylic acid 2-hydroxyamide 5-({1-[5-(4-trifluoromethyl-phenyl)-isoxazol-3-yl]-ethyl}-amide).

Another preferred embodiment of the invention are the (R)- or (S)-enantiomers or racemates of the compounds of formula Ia

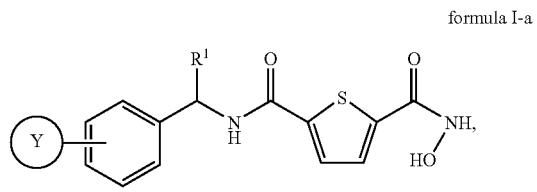

formula I-a wherein
R$^1$ is alkyl, which is optionally substituted one or several times by halogen;
Y is a saturated carbocyclic group;
a saturated heterocyclic group;
a heteroaryl group; or
a substituted phenyl group,
and all pharmaceutically acceptable salts thereof Another embodiment of the invention are the (R)- or (S)-enantiomers or racemates of the compounds of formula I-a, wherein
Y is a saturated carbocyclic group.

Such a compound is for example:
Thiophene-2,5-dicarboxylic acid 2-{[1-(4-cyclohexyl-phenyl)-ethyl]-amide}5-hydroxyamide Still another preferred embodiment of the invention are the (R)- or (S)-enantiomers or racemates of the compounds of formula I-a, wherein
Y is a saturated heterocyclic group.

Such compounds are for example:
(R)-Thiophene-2,5-dicarboxylic acid 2-hydroxyamide 5-{[1-(4-morpholin-4-yl-phenyl)-ethyl]-amide};
Thiophene-2,5-dicarboxylic acid 2-hydroxyamide 5-{[1-(4-piperidin-1-yl-phenyl)-ethyl]-amide}; and
Thiophene-2,5-dicarboxylic acid 2-hydroxyamide 5-({1-[4-(4-methyl-piperazin-1-yl)-phenyl]-ethyl}-amide); acetic acid salt.

Yet another preferred embodiment of the invention are the (R)- or (S)-enantiomers or racemates of the compounds of formula I-a, wherein
Y is a heteroaryl group.

Such compounds are for example:
(R)-Thiophene-2,5-dicarboxylic acid 2-hydroxyamide 5-{[1-(4-thiophen-2-yl-phenyl)-ethyl]-amide};
(R)-Thiophene-2,5-dicarboxylic acid 2-hydroxyamide 5-({1-[4-(5-methyl-thiophen-2-yl)-phenyl]-ethyl}-amide);
Thiophene-2,5-dicarboxylic acid 2-hydroxyamide 5-({1-[4-(1H-pyrazol-4-yl)-phenyl]-ethyl}-amide);

Thiophene-2,5-dicarboxylic acid 2-hydroxyamide 5-{[1-(3-thiophen-2-yl-phenyl)-ethyl]-amide};

Thiophene-2,5-dicarboxylic acid 2-{[1-(3-benzo[b]thiophen-2-yl-phenyl)-ethyl]-amide}5-hydroxyamide;

Thiophene-2,5-dicarboxylic acid 2-hydroxyamide 5-({1-[3-(5-methyl-thiophen-2-yl)-phenyl]-ethyl}-amide);

Thiophene-2,5-dicarboxylic acid 2-hydroxyamide 5-({1-[3-(1H-pyrazol-4-yl)-phenyl]-ethyl}-amide);

Thiophene-2,5-dicarboxylic acid 2-({1-[3-(3,5-dimethyl-isoxazol-4-yl)-phenyl]-ethyl}-amide) 5-hydroxyamide;

Thiophene-2,5-dicarboxylic acid 2-hydroxyamide 5-({1-[3-(1H-indol-5-yl)-phenyl]-ethyl}-amide);

Thiophene-2,5-dicarboxylic acid 2-hydroxyamide 5-{[1-(3-pyridin-3-yl-phenyl)-ethyl]-amide}; and Thiophene-2,5-dicarboxylic acid 2-hydroxyamide 5-{[1-(4-imidazol-1-yl-phenyl)-ethyl]-amide}.

Another embodiment of the invention are the (R)- or (S)-enantiomers or racemates of the compounds of formula I-a, wherein Y is a substituted phenyl group.

Such compounds are for example:

Thiophene-2,5-dicarboxylic acid 2-{[1-(4'-dimethylamino-biphenyl-4-yl)-ethyl]-amide}5-hydroxyamide;

(R)-Thiophene-2,5-dicarboxylic acid 2-hydroxyamide 5-{[1-(3',4',5'-trifluoro-biphenyl-4-yl)-ethyl]-amide};

(R)-Thiophene-2,5-dicarboxylic acid 2-hydroxyamide 5-{[1-(2'-methoxy-biphenyl-4-yl)-ethyl]-amide};

(R)-Thiophene-2,5-dicarboxylic acid 2-hydroxyamide 5-{[1-(2'-methyl-biphenyl-4-yl)-ethyl]-amide};

(R)-Thiophene-2,5-dicarboxylic acid 2-{[1-(2'-fluoro-biphenyl-4-yl)-ethyl]-amide}5-hydroxyamide;

(R)-Thiophene-2,5-dicarboxylic acid 2-{[1-(3'-fluoro-biphenyl-4-yl)-ethyl]-amide}5-hydroxyamide;

(R)-Thiophene-2,5-dicarboxylic acid 2-hydroxyamide 5-{[1-(3'-methyl-biphenyl-4-yl)-ethyl]-amide};

(R)-Thiophene-2,5-dicarboxylic acid 2-hydroxyamide 5-{[1-(3'-methoxy-biphenyl-4-yl)-ethyl]-amide};

Thiophene-2,5-dicarboxylic acid 2-{[1-(4'-chloro-biphenyl-3-yl)-ethyl]-amide}5-hydroxyamide;

Thiophene-2,5-dicarboxylic acid 2-hydroxyamide 5-{[1-(2'-methoxy-biphenyl-3-yl)-ethyl]-amide};

Thiophene-2,5-dicarboxylic acid 2-hydroxyamide 5-{[1-(2'-methyl-biphenyl-3-yl)-ethyl]-amide};

Thiophene-2,5-dicarboxylic acid 2-hydroxyamide 5-{[1-(4'-methoxy-biphenyl-3-yl)-ethyl]-amide};

Thiophene-2,5-dicarboxylic acid 2-{[1-(4'-dimethylamino-biphenyl-3-yl)-ethyl]-amide}5-hydroxyamide;

Thiophene-2,5-dicarboxylic acid 2-{[1-(2'-fluoro-biphenyl-3-yl)-ethyl]-amide}5-hydroxyamide;

Thiophene-2,5-dicarboxylic acid 2-{[1-(4'-fluoro-biphenyl-3-yl)-ethyl]-amide}5-hydroxyamide;

Thiophene-2,5-dicarboxylic acid 2-{[1-(3'-fluoro-biphenyl-3-yl)-ethyl]-amide}5-hydroxyamide;

Thiophene-2,5-dicarboxylic acid 2-hydroxyamide 5-{[1-(4'-methyl-biphenyl-3-yl)-ethyl]-amide};

Thiophene-2,5-dicarboxylic acid 2-{[1-(2'-chloro-biphenyl-3-yl)-ethyl]-amide}5-hydroxyamide;

Thiophene-2,5-dicarboxylic acid 2-{[1-(3'-chloro-biphenyl-3-yl)-ethyl]-amide}5-hydroxyamide;

Thiophene-2,5-dicarboxylic acid 2-hydroxyamide 5-{[1-(3'-methyl-biphenyl-3-yl)-ethyl]-amide};

Thiophene-2,5-dicarboxylic acid 2-hydroxyamide 5-{[1-(3'-methoxy-biphenyl-3-yl)-ethyl]-amide}; and Thiophene-2,5-dicarboxylic acid 2-hydroxyamide 5-{[1-(4'-methanesulfonyl-biphenyl-3-yl)-ethyl]-amide}.

A further embodiment of the invention are the (R)- or (S)-enantiomers or racemates of the compounds of formula I-b

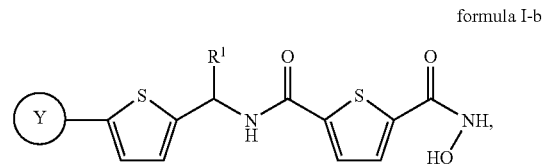

formula I-b wherein

R$^1$ is alkyl, which is optionally substituted one or several times by halogen;

Y is a saturated carbocyclic group;
a saturated heterocyclic group;
a heteroaryl group; or
a substituted phenyl group, and all pharmaceutically acceptable salts thereof.

Another embodiment of the invention are the (R)- or (S)-enantiomers or racemates of the compounds of formula I-b, wherein Y is a saturated carbocyclic group.

Still another embodiment of the invention are the (R)- or (S)-enantiomers or racemates of the compounds of formula I-b, wherein Y is a saturated heterocyclic group.

Yet another embodiment of the invention are the (R)- or (S)-enantiomers or racemates of the compounds of formula I-b, wherein Y is a heteroaryl group.

Such compounds are for example:

Thiophene-2,5-dicarboxylic acid 2-{[1-(5-benzo [b]thiophen-2-yl-thiophen-2-yl)-ethyl]-amide}5-hydroxyamide;

Thiophene-2,5-dicarboxylic acid 2-({1-[5-(3,5-dimethyl-isoxazol-4-yl)-thiophen-2-yl]-ethyl}-amide)5-hydroxyamide;

Thiophene-2,5-dicarboxylic acid 2-hydroxyamide 5-({1-[5-(1H-indol-5-yl)-thiophen-2-yl]-ethyl}-amide); and Thiophene-2,5-dicarboxylic acid 2-hydroxyamide 5-{[1-(5-pyridin-3-yl-thiophen-2-yl)-ethyl]-amide}.

Another embodiment of the invention are the (R)- or (S)-enantiomers or racemates of the compounds of formula I-b, wherein Y is a substituted phenyl group.

Such compounds are for example:

Thiophene-2,5-dicarboxylic acid 2-hydroxyamide 5-({1-[5-(2-methoxy-phenyl)-thiophen-2-yl]-ethyl}-amide);

Thiophene-2,5-dicarboxylic acid 2-({1-[5-(4-dimethylamino-phenyl)-thiophen-2-yl]-ethyl}-amide)5-hydroxyamide;

Thiophene-2,5-dicarboxylic acid 2-hydroxyamide 5-{[1-(5-o-tolyl-thiophen-2-yl)-ethyl]-amide};

Thiophene-2,5-dicarboxylic acid 2-hydroxyamide 5-{[1-(5-m-tolyl-thiophen-2-yl)-ethyl]-amide};

Thiophene-2,5-dicarboxylic acid 2-hydroxyamide 5-{[1-(5-p-tolyl-thiophen-2-yl)-ethyl]-amide};

Thiophene-2,5-dicarboxylic acid 2-({1-[5-(2-chloro-phenyl)-thiophen-2-yl]-ethyl}-amide) 5-hydroxyamide;

Thiophene-2,5-dicarboxylic acid 2-hydroxyamide 5-({1-[5-(4-methoxy-phenyl)-thiophen-2-yl]-ethyl}-amide);

Thiophene-2,5-dicarboxylic acid 2-({1-[5-(4-fluoro-phenyl)-thiophen-2-yl]-ethyl}-amide) 5-hydroxyamide;

Thiophene-2,5-dicarboxylic acid 2-({1-[5-(3-fluoro-phenyl)-thiophen-2-yl]-ethyl}-amide) 5-hydroxyamide;

Thiophene-2,5-dicarboxylic acid 2-({1-[5-(4-chloro-phenyl)-thiophen-2-yl]-ethyl}-amide) 5-hydroxyamide;

Thiophene-2,5-dicarboxylic acid 2-({1-[5-(3-chloro-phenyl)-thiophen-2-yl]-ethyl}-amide) 5-hydroxyamide;

Thiophene-2,5-dicarboxylic acid 2-({1-[5-(2-fluoro-phenyl)-thiophen-2-yl]-ethyl}-amide) 5-hydroxyamide;

Thiophene-2,5-dicarboxylic acid 2-hydroxyamide 5-({1-[5-(3-methoxy-phenyl)-thiophen-2-yl]-ethyl}-amide); and Thiophene-2,5-dicarboxylic acid 2-hydroxyamide 5-({1-[5-(4-methanesulfonyl-phenyl)-thiophen-2-yl]-ethyl}-amide).

Yet another embodiment of the invention is the process for the manufacture of the compounds of formula I, especially their (R)- and (S) enantiomers, by reacting a compound of formula IV

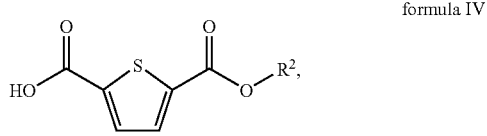

formula IV wherein
$R^2$ is an alkyl group;
with an racemic, or enantiomerically pure (R)- or (S)-amine of the formula VII

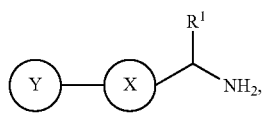

formula VII wherein
X, Y and $R^1$ have the meaning given hereinabove for formula I,
in the presence of a suitable activating agent,
to give a compound of formula VIII

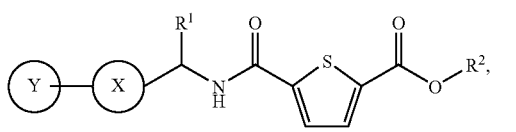

formula VIII which is treated with hydroxylamine to give the respective compound of formula I; and if desired, transforming said compound into its pharmaceutically acceptable salt.

Still another embodiment of the invention is the process for the manufacture of the compounds of formula I, especially their (R)- and (S) enantiomers, by reacting a compound of formula IV

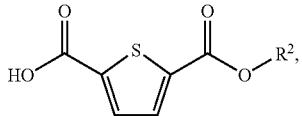

formula IV wherein
$R^2$ is an alkyl group;
with an racemic, or enantiomerically pure (R)- or (S)-amine of the formula III

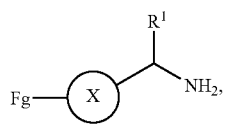

formula III wherein
X and $R^1$ have the meaning given hereinabove for formula I, and Fg represents a functional group suitable for cross-coupling reactions like halogen, triflate, —ZnCl, boronic acids, boronic acid pinacolesters and trialkylstannanes (e.g. Me3Sn, Bu3Sn). (see also section (3-1), scheme 1).
in the presence of a suitable activating agent,
to give a compound of formula V

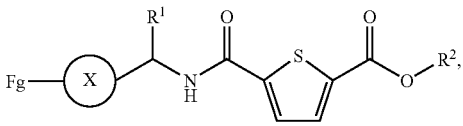

formula V which is reacted with a compound of formula X

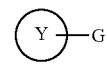

formula X wherein Y has the meaning as defined above for formula I and G represents the a functional group suitable for cross-coupling reactions (compatible with Fg) like halogen, triflate, —ZnCl, boronic acids, boronic acid pinacolesters and trialkylstannanes (e.g. Me3Sn, Bu3Sn). (see also section (3-1), scheme 1), and subsequently treated with hydroxylamine to give the respective compound of formula I; and if desired, transforming said compound into its pharmaceutically acceptable salt.

The present compounds of formula I, or a pharmaceutically acceptable salt thereof, may be prepared by any process known to be applicable to the preparation of chemically-related compounds. Such processes, when used to prepare a thiophene derivative of the formula I, or a pharmaceutically-acceptable salt thereof, are illustrated by the following representative examples in which, unless otherwise stated, Y, X and $R^1$ have any of the meanings defined hereinbefore.

Necessary starting materials may be obtained by standard procedures of organic chemistry. The preparation of such starting materials is described within the accompanying examples. Alternatively necessary starting materials are obtainable by analogous procedures to those illustrated which are within the ordinary skill of an organic chemist.

In the following scheme 1 several methods for the manufacture of the compounds of formula I are illustrated.

reaction vessel. The reaction mixture usually contains a source of ammonia for example NH4OAc and a reducing agent for example sodium cyanoborohydride and is heated in a suitable solvent e.g. methanol.

(1-2) Another method for the preparation of amines of general formula VII, which is not shown in scheme 1 is the addition of a Grignard reagent $R^1$—MgBr or an organo-

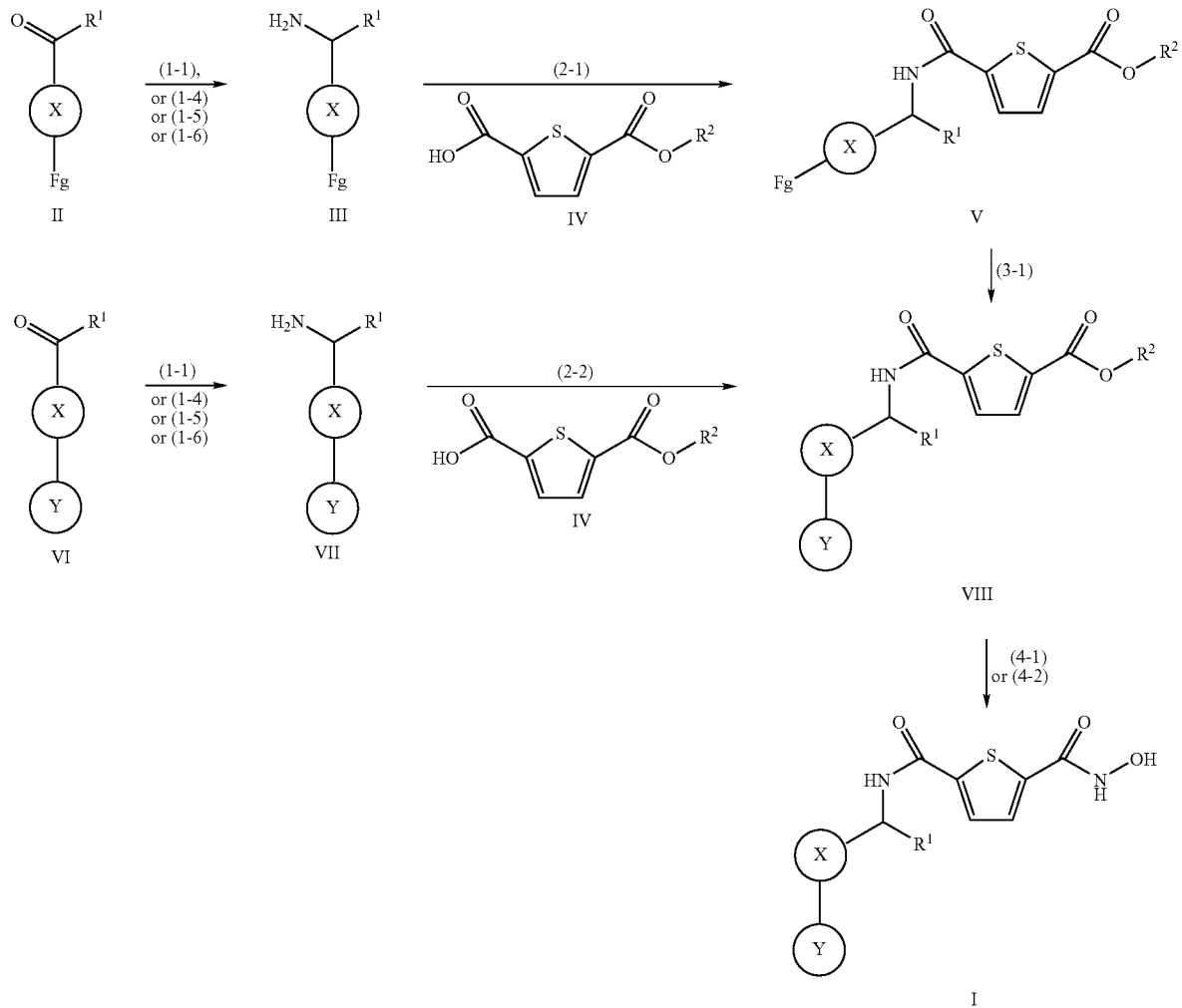

In scheme 1, $R^1$ is defined as for formula I and $R^3$ is alkyl or optionally substituted benzyl. Fg means a functional group suitable for cross-coupling reactions like halogen, triflate, —ZnCl, boronic acids, boronic acid pinacolesters and tri-alkylstannanes (e.g. Me$_3$Sn, Bu$_3$Sn).

(1-1) Some of the amines of the general formulas VII or III, wherein Y, X and R1 have the meaning defined hereinbefore and Fg represents a suitable functional group as described above, are commercially available. They can also be prepared for example by reductive amination of the corresponding ketones of general formulas VI and II.

This reductive amination reaction is typically carried out as a one-pot reaction with the formation of the imine and its subsequent reduction to the amine taking place in the same lithium compounds Li—R1 with $R^1$ as defined above to an aromatic nitrile of the general formula IX formula IX

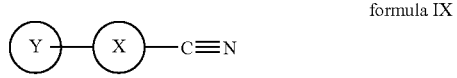

wherein ring X and Y are defined as above and subsequent reduction of the imine (Synth. Commun. 1998, 28(21), 4067).

(1-3) Amines of the general formula VII, wherein X=isoxazolediyl, Y=substituted phenyl group and $R^1$=methyl can for example be prepared from suitably phenyl substituted acetophenones via a mixed Claisen condensation with diethyl oxalate and subsequent ring closure to form the isoxazole ring with hydroxylamine (Baraldi, P. G., et al., J. Heterocyclic Chem. 19 (1982) 557-560). The ester of the 5-phenyl-isoxazole-3-carboxylic acid ethyl ester is reacted with methyl magnesium bromide to form the methyl ketone (Kikkawa, I., et al., Synthesis 11 (1980) 877) which in turn is subjected to a reductive amination as described in section (1-1).

Pure (R)- and (S)-enantiomers of amines of the formulas VII or III in which Y, X, $R^1$ and Fg have the meaning defined hereinbefore are commercially available or can be prepared from commercially available optionally enantiomerically pure precursors by standard procedures of organic chemistry.

(1-4) A preferred method to introduce the chiral center of amines of the formulas VII or III is for example the enantioselective reduction of the corresponding arylalkylketones of formulas VI or II. This reduction can be accomplished e.g. with a combination of the chiral CBS (Corey, Bakshi, Shibata) reagent and the borane-THF complex, the borane-diethylaniline complex or the borane-dimethylsulfide as the reducing agent (Corey, E. J., et al., Angew. Chemie 110 (1998) 2092-2118). Yet another preferred method for the enantioselective reduction of arylalkylketones of formulas VI or II employs diisopinocampheylchloroborane in a suitable solvent e.g. THF and subsequent work up with e.g. H2O2/NaHCO3 or diethanolamine (Brown, H. C., et al., J. Am. Chem. Soc. 110 (1988) 1539-1546; Wiegers, A., and Scharf, H. D., Tetr. Asym. 7 (1996) 2303-2312). Another preferred method is the asymmetric catalytic hydrogenation of the arylalkylketones of formulas VI or II in the presence of transition metal catalyst with chiral ligands of Noyori type (Noyori, R., et al., Angew. Chem. 113 (2001) 40-75). The chiral alcohols that are obtained in these enantioselective reductions of the arylalkylketones of formulas VI or II can then be converted to the amines of formulas VII or III by standard procedures of synthetic chemistry as described e.g. in Chen, C.-P., et al., Tetrahedron Lett. 32 (1991) 7175-7178: displacement of the hydroxy group with a nitrogen functionality (for example with azide or with phthalimide) under Mitsunobu conditions (Mitsunobu, O., Synthesis 1 (1981) 1-28) and subsequent conversion to the amine (e.g. reduction of the azide with triphenylphosphine or catalytic hydrogenation (Pd/C, H2, CF3COOH) or hydrazinolysis of the phthalimide). (1-5) Racemic amines of the formulas VII or III in which Y, X, $R^1$, Fg have the meaning defined hereinbefore can be separated into their enantiomers by known procedures as, for example, fractional crystallization of the diastereomeric salts that are formed with suitable chiral enantiomerically pure acids (Smith, H. E., et al., J. Am. Chem. Soc. 105 (1983) 1578; U.S. Pat. No. 4,983,771). These acids may be commercially available, e.g. mandelic acid, tartaric acid, lactic acid, camphoric acid, camphorsulfonic acid, N-acetylleucine, dibenzoyltartaric acid or they are especially designed for the resolution of 1-arylethylamines for example 2-naphtylglycolic acid (Kinbara, K., et al., J. Chem. Soc., Perkin Trans. 2 (2000) 1339-1348) or isopropylidene glycerol 3-carboxy-2-naphtoate (Pallavicini, M., et al., Tetr. Asym. 12 (2001) 2489-2495)

(1-6) Another preferred method for the separation of the two enantiomers of racemic amines of the formulas VII or III is the enzyme catalyzed resolution, for example with lipase from candida Antarctica B (Rasor, J. P., and Voss, E., Applied Catalysis A: General 221 (2001) 145-195; Iglesias, L. E., et al., Tetr.Asym. 8 (1997) 2675-2677)

(1-7) Another method for the asymmetric preparation of 1-(aryl)ethylamines is the nucleophilic addition of methyl lithium to chiral oxime ethers (Yamazaki, N., et al., Tetrahedron Lett. 42 (2001) 5029-5032) and subsequent conversion to the amine.

(2-1) Compounds of the general formula V, wherein Y, X, Fg and $R^1$ have the meaning defined hereinbefore can be obtained by the reaction of compounds of formula IV wherein $R^2$ is a $(C_1-C_4)$alkyl group, preferably a methyl, ethyl or t-butyl group or an optionally substituted benzyl group with an amine of the formula III wherein Fg, X and $R^1$ have the meaning defined hereinbefore. This reaction typically involves a two-step one-pot procedure.

In the first step, the carboxylic acid of the formula IV becomes activated. The activation reaction is carried out in an inert solvent or diluent, for example, in dichloromethane, dioxane, or tetrahydrofuran, in the presence of an activating agent. Such activated acid derivatives are, for example, an acyl halide (e.g. acyl chloride) formed by the reaction of the acid and an inorganic acid chloride, (e.g. thionyl chloride); a mixed anhydride, formed for example by the reaction of the acid and a chloroformate (e.g. isobutyl chloroformate); an active ester, formed for example by the reaction of the acid and a phenol (e.g. pentafluorophenol); an active ester, formed by the reaction of the acid and N-hydroxybenzotriazole; an acyl azide, formed for example by the reaction of the acid and an azide (e.g. diphenylphosphoryl azide); an acyl cyanide, formed for example by the reaction of an acid and a cyanide (e.g. diethylphosphoryl cyanide); or the product of the reaction of the acid and a carbodiimide (e.g. dicyclohexylcarbodiimide), or the product of the reaction of the acid and bis-(2-oxo-3-oxazolidinyl)-phosphorylchloride. The reaction is carried out between –30° C. and 60° C., conventionally at or below 0° C.

In the second step, the amine of the general formula III, in which $R^1$ has the meaning defined hereinbefore, is added to the solution, at the temperature used for the activation, and the temperature is slowly adjusted to ambient temperature. An appropriate scavenger base like e.g. triethylamine, or diisopropylethylamine may be added to the reaction mixture. These methods are well known to those skilled in the art. In principle, all methods for the synthesis of amides as used in peptide chemistry as described in e.g. Houben-Weyl, "Methoden der organischen Chemie", Vols. XV/1 and XV/2, Georg Thieme Verlag, Stuttgart, are also applicable.

Compounds of formula IV are described in the literature as for example in U.S. Pat. No. 2,680,731 and J. Heterocycl. Chem. 28 (1991) 17. These monoesters are usually prepared by selective saponification of the diester or oxidation of the corresponding aldehyde, but other methods may be useful as well and are well known to those skilled in the art.

The functional group Fg in formula III (and in the corresponding formula II) might bear a protecting group prior to the reaction of amines of formula III with compounds of formula IV and has to be liberated thereafter for further transformations.

(2-2) In analogy to the section (2-1) the compounds of formula VIII wherein Y, X, $R^1$ and $R^2$ have the meaning defined hereinbefore can be prepared from compounds of formula IV wherein $R^2$ has the meaning defined hereinbefore by reaction with an amine of formula VII. The reaction can be carried out under conditions as described for the preparation of compounds of formula IV in section (2-1).

(3-1) One method for the preparation of compounds of the formula VIII involves reaction of compounds of formula V wherein X, $R^1$, $R^2$ and Fg have the meaning as defined above and Fg represents a functional group suitable for cross-coupling reactions as described above.

a) Compounds of the formula VIII with Y is a substituted phenyl group or heteroaryl group can be prepared by a palladium catalysed cross coupling reaction between V wherein Y, R¹ and R² have the meaning defined hereinbefore and Fg represents a suitable functional group as described above and a compound of the general formula X

formula X wherein ring Y has the meaning as defined above and G represents a functional group suitable for cross-coupling reactions, and compatible with Fg, as described above.

This palladium catalyzed cross coupling reaction may be for example, but not limited to, of Suzuki type (G is boronic acid, boronic acid pinacolester etc. and Fg is halogen or Fg is boronic acids, boronic acid pinacolester etc. and G is halogen; see e.g. Miyaura, N., et al., Chem. Rev. 95 (1995) 2457-2483; Miyaura, N., et al., Synth. Commun. 11 (1981) 513-519), of Negishi type (G is ZnCl etc. and Fg is halogen or Fg is ZnCl etc. and G is halogen; see e.g. Negishi, E., et al., J. Org. Chem. 42 (1977) 1821-1823) or of Stille type (G is trialkylstannane e.g. Me3Sn, Bu3Sn and Fg is triflate, halogen or Fg is trialkylstannane e.g. Me3Sn, Bu3Sn and G is triflate, halogen; see e.g. Stille, J. K., Angew. Chem. 98 (1986) 504).

The intermediates of formulas V, III or II wherein Fg is a boronic acid, a boronic acid pinacolesters or trialkylstannane etc., can be obtained for example from the corresponding halogenides (Fg is halogen) by standard procedures of organic chemistry. For example compounds of formula V, III or II wherein Fg is a boronic acid pinacolester can be prepared from the bromide by a palladium catalyzed (e.g. PdCl2 (dppf)-CH2Cl2-complex) coupling with pinacolboran or bis (pinacolato)diboron. For example compounds of formula V wherein Fg is trialkylstannane can be prepared from the bromide by a palladium catalyzed (e.g. PdCl2(MeCN)2-Komplex) coupling with hexa-alkylditin.

b) Compounds of the formula VIII, wherein Y is a saturated heterocyclic amine or a N-containing heteroaryl group, can be prepared by a palladium catalyzed cross coupling reaction between a compound of formula V and a compound of formula XI

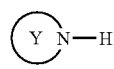

formula XI wherein the H-atom is bonded to a N-atom of the ring Y.

This reaction may be for example, but not limited to, of Buchwald-Hartwig type and related reactions (Fg is iodide, bromide, triflate or chloride; see e.g. Kwong, F. Y., et al., Org. Lett. 4 (2002) 581-584; Louie, J., et al., J. Org. Chem. 62 (1997) 1268-1273; Wolfe, J. P., et al., J. Am. Chem. Soc. 119 (1997) 6054-6058; Yin, J., et al., Org. Lett. 4 (2002) 3481-3484; Mann, G., et al., J. Am. Chem. Soc. 120 (1998) 827-828).

Another preferred method is a palladium catalyzed cross coupling reaction between compounds of formula X and an arylboronic acid of formula V wherein Fg is B(OH)2 (see e.g. Chan, D. M. T., et al., Tetrahedron Lett. 39 (1998) 2933-2936; Lam, P. Y. S., et al., Tetrahedron Lett. 39 (1998) 2941-2944)

(4-1) One method for the production of compounds of the formula I involves the reaction of compounds of the formula VIII, wherein Y, X and R¹ have the meaning defined hereinbefore and R² is a (C₁-C₄)alkyl group, preferably a methyl, ethyl or t-butyl group or an optionally substituted benzyl group, with hydroxylamine in the presence of a suitable base. The reaction is carried out in an inert solvent or diluent such as methanol or ethanol at temperatures between 0° C. and 100° C., conventionally at or near ambient temperature, and at a pH between 10 and 12. A suitable base is, for example, an alcoholate, for example, sodium methylate. Instead of generating hydroxylamine in situ, it can be released separately and can be applied as a solution in an organic solvent, as for example an alcohol like methanol or ethanol.

(4-2) Another method for the preparation of compounds of the formula I is a reaction sequence via carboxylic acids of formula XII

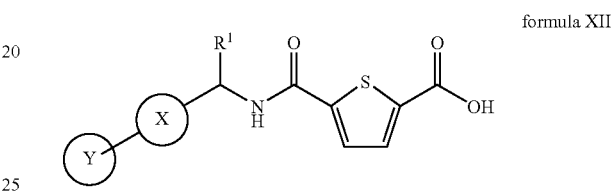

formula XII wherein Y, X, R¹ have the meaning as defined hereinabove.

These intermediates of formula XII are prepared from compounds of the formula VIII by hydrolysis. The conditions under which the hydrolysis is carried out depend on the nature of the group R². When R² is a methyl or ethyl group, the reaction is carried out in the presence of a base, for example, lithium hydroxide, sodium hydroxide, or potassium hydroxide in an inert solvent or diluent, for example, in methanol or ethanol. When R² is a tert-butyl group, the reaction is carried out in the presence of an acid, for example, a solution of hydrochloric acid in an inert solvent such as diethyl ether or dioxane, or trifluoroacetic acid in dichloromethane. When R² is a benzyl group, the reaction is carried out by hydrogenolysis in the presence of a noble metal catalyst such as palladium or platinum on a suitable carrier, such as activated carbon. Not necessarily all methods of hydrolysis are compatible with all groups Y, X, or R¹. In cases where the features of these groups do not allow the usage of a certain method of hydrolysis, other methods of preparation need to be applied.

Subsequent reaction of the acids of formula XII with hydroxylamine yields the compounds of formula I. This reaction typically involves a two-step one-pot procedure.

In the first step, the carboxylic acid of the formula XII becomes activated. The activation reaction is carried out in an inert solvent or diluent, for example, in dichloromethane, dioxane, or tetrahydrofuran, in the presence of an activating agent. Such activated acid derivatives are, for example, an acyl halide (e.g. acyl chloride) formed by the reaction of the acid and an inorganic acid chloride, (e.g. thionyl chloride); a mixed anhydride, formed for example by the reaction of the acid and a chloroformate (e.g. isobutyl chloroformate); an active ester, formed for example by the reaction of the acid and a phenol (e.g. pentafluorophenol); an active ester, formed by the reaction of the acid and N-hydroxybenzotriazole; an acyl azide, formed for example by the reaction of the acid and an azide (e.g. diphenylphosphoryl azide); an acyl cyanide, formed for example by the reaction of an acid and a cyanide (e.g. diethylphosphoryl cyanide); or the product of the reaction of the acid and a carbodiimide (e.g. dicyclohexylcarbodiimide), or the product of the reaction of the acid and bis- (2-oxo-3-oxazolidinyl)-phosphorylchloride. The reaction is carried out between −30° C. and 60° C., conventionally at or below 0° C.

In the second step, hydroxylamine is added to the solution, at the temperature used for the activation, and the temperature is slowly adjusted to ambient temperature. These methods are well known to those skilled in the art. In principle, all methods for the synthesis of amides as used in peptide chemistry as described in e.g. Houben-Weyl, "Methoden der organischen Chemie", Vols. XV/1 and XV/2 are also applicable.

Compounds of the formula XII are new and also subject of the present invention.

In the following further methods for the preparation of compounds I, which are not explicitly shown in scheme 1, are described.

One alternative route for the preparation of compounds of the formula I is the introduction of O-protecting groups Q for the hydroxamic acid moiety of compounds of formula I and a deprotection in the final reaction step to liberate the compounds of formula I.

Suitable O-protecting groups Q may be the benzyl-, p-methoxybenzyl-, tert-butyloxycarbonyl-, trityl-, or silyl groups such as the trimethylsilyl- or dimethyl-tert-butylsilyl-group.

To introduce these protecting groups into intermediates V or VIII, an analogous reaction route as described in section (4-2) can be chosen. First step is an hydrolysis to the corresponding carboxylic acids, which are activated and reacted with Q—O—NH$_2$ to the desired O-protected hydroxamates.

The final deprotection reactions carried out depend on the type of the protecting group. When the protecting group is a benzyl- or p-methoxybenzyl group, the reaction carried out is a hydrogenolysis in an inert solvent such as an alcohol like methanol or ethanol, in the presence of a noble metal catalyst such as palladium on a suitable carrier such as carbon, barium sulfate, or barium carbonate, at ambient temperature and pressure. When the protecting group is the tert-butyloxycarbonyl-, trityl-, or a silyl group such as the trimethylsilyl- or dimethyl-tert-butylsilyl-group, the reaction is carried out in the presence of acids at a temperature between −20° C. and 60° C., preferably between 0° C. and ambient temperature. The acid may be a solution of hydrochloric acid in an inert solvent such as diethyl ether or dioxane, or trifluoro acetic acid in dichloromethane. When the protecting group is a silyl group such as the trimethylsilyl or dimethyl-tert-butylsilyl group, the reaction can also be carried out in the presence of a fluoride source such as sodium fluoride or tetrabutyl ammonium fluoride in an inert solvent such as dichloromethane. Not necessarily all protecting groups Q are compatible with all groups Y, X and R1. In cases where the features of these groups don't allow the usage of a certain protecting group, other protecting groups Q or other methods of preparation need to be applied.

Compounds of formula I can also be prepared with methods of solid phase supported synthesis. 2,5-thiophenedicarboxylic acid is reacted with a hydroxylamine moiety (—O—NH$_2$) bound to a resin, e.g. hydroxylamine Wang resin or hydroxylamine 2-chlorotrityl resin to form a resin-bound hydroxamic acid. The second carboxylic acid moiety is reacted with an amine of formula VII or III, wherein Y, X and R$^1$ have the meaning defined hereinbefore and Fg represents a suitable functional group as described hereinbefore, by standard methods of amide bond formation as described in e.g. Houben-Weyl, "Methoden der organischen Chemie", Vols. XV/1 and XV/2. Optionally, the present functional group Fg is reacted with a compound of the general formula X, wherein ring Y has the meaning as described hereinbefore and G represents a suitable functional group as defined above. This can be done as described in section (3-1).

After this, the hydroxamic acid is liberated from the solid support. This can be done for example with TFA. Typically, the cleavage of the hydroxamic acids is achieved by treatment of the resin with 50% TFA in dichloromethane in the presence of triisopropyl silane at ambient temperature. The crude products can be purified by LC-MS, if necessary.

A method for the production of pure (R)-and (S)-enantiomers of formula I includes the employment of enantiomerically pure amines of formulas VII or III within the synthesis of the compounds of formula I as described above in section (1-4) to (1-7).

Yet another method for the preparation of pure (R)-and (S)-enantiomers of compounds of formula I is the synthesis of racemic compounds according to methods (1-1) to (4-2). The racemates can be separated subsequently into both enantiomers on either the stage of the final products or the precursors of formula VIII. The separation can be performed by chromatography on an analytical, semipreparative or preparative scale using suitable optically active stationary phases with suitable eluents. Suitable optically active stationary phases include, but are not limited to, silica (e.g. ChiraSper, Merck; Chiralpak OT/OP, Baker), cellulose or amylose esters or carbamates (e.g. Chiralpak AD, Daicel Chemical Industries Ltd.; Chiracel OD-CSP, Daicel; Chiracel OB/OY, Baker) or others (e.g. Crownpak, Daicel or Chiracel OJ-R, Baker). Suitable eluents include, but are not limited to hexane, heptane, ethanol, isopropanol, acetonitrile, water and mixtures thereof Other methods for the separation of enantiomers can also be applied, like the formation of diastereomeric compounds from compounds of the formula I together with other optically active compounds, e.g. camphorsulfonic acid or brucin, and separation of these diastereomeric compounds, followed by the liberation from the optically active agent.

An object of the present invention are pharmaceutical compositions containing a pharmacologically effective amount of one or more enantiomerically pure compounds of formula I in a mixture with pharmaceutically acceptable excipients and/or diluents.

According to a further aspect of the invention there is provided a medicament containing one or more enantiomerically pure compounds of the formula I as active ingredients together with pharmaceutically acceptable adjuvants. Such medicaments or pharmaceutical compositions may be in a form suitable for oral administration, for example as tablets, coated tablets, dragées, capsules, solutions emulsions or suspensions; for parenteral injections (including intravenous, subcutaneous, intramuscular, intravascular or infusion) as a sterile solution, suspension or emulsion; for topical administration as an ointment or cream or for rectal administration as a suppository. These pharmaceutical preparations can be obtained by processing the compounds according to this invention with pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Pharmaceutical compositions can comprise the following:

| Item | Ingredients | Mg/Tablet | |
|---|---|---|---|
| 1 | Compound of formula (I) | 25 | 100 |
| 2 | Anhydrous Lactose | 73 | 35 |
| 3 | Croscarmellose Sodium | 6 | 8 |
| 4 | Povidone K30 | 5 | 6 |
| 5 | Magnesium Stearate | 1 | 1 |
| | Total Weight | 140 | 150 |

Procedure:
1. Mix Items 1, 2 and 3 in a suitable mixer for 15 minutes.
2. Granulate the powder mix from Step 1 with 20% Povidone K30 Solution (Item 4).
3. Dry the granulation from Step 2 at 50° C.
4. Pass the granulation from Step 3 though a suitable milling equipment.
5. Add the Item 5 to the milled granulation Step 4 and mix for 3 minutes.
6. Compress the granulation from Step 5 on a suitable press.

Another pharmaceutical preparation is e.g. a micro-suspension of the compounds according to formula I. To obtain said micro-suspension the following materials were used:

An aqueous solution of 7.5% modified gelatine XF 20 (Braun) per injection (dissolved, filtered with a pore size of 0.45 μm and autoclaved), filters (custom made, mesh size 100 μm), filter holder, coupling, washed glass beads with a diameter of 0.25 mm and heat sterilised Retsch mills.

For the preparation of a typical batch 6244 mg of a compound of formula (I) were weighted into two 50 ml bottle flasks with 30 g glass beads, dispersed with a spatulum and vortexed. Then 10 ml gelatine vehicle were added to each bottle. The bottles were vortexed, capped and wrapped in aluminium foil for light protection. The contents was milled for 14 hours at 30/s in a Retsch mill. The micro-suspension was then extracted from the beads with two layers of filter (100 μm) on a filter holder, coupled to a recipient vial by centrifugation at 400 g during two minutes and including six washing steps, to give a final volume of 130 ml.

After homogenisation, the content was determined by HPLC to be 45.7 mg/ml which corresponds to a yield of 95%. The micro-suspension was diluted with 18.6 ml to give a final concentration of 40 mg/ml. The obtained spherical, granule-like particles show diameters between 1 and 5 μm as determined by microscopy. For storage, the micro-suspension was filled into sterile vials, capped, labelled and kept at −20° C. Before use, the micro-suspension must be homogenised vigorously by vortex.

The thiophene derivative will normally be administered to a warm-blooded animal at a unit dose within the range 5-5000 mg per square meter body area of the animal, i.e. approximately 0.1-100 mg/kg, and this normally provides a therapeutically-effective dose. A unit dose form such as a tablet or capsule will usually contain, for example 1-250 mg of active ingredient. Preferably a daily dose in the range of 1-100 mg/kg is employed. However the daily dose will necessarily be varied depending upon the host treated, the particular route of administration, and the severity of the illness being treated. Accordingly the optimum dosage may be determined by the practitioner who is treating any particular patient.

Pharmacological Activity

To show the activity of the compounds according to this invention, their effects on a human colon carcinoma cell line was evaluated using a standard MTT-assay. MTT (3-(4,5-dimethylthiazol-2-yl)-2,5-diphenyl tetrazolium bromide) is widely used for the quantitative determination of cytotoxic effects or in vitro chemosensitivity of tumor cells. The assay is based on the cleavage of the yellow tetrazolium salt (MTT) to purple formazan crystals by metabolic active cells. For details, see Rubinstein, L. V., et al., J. Natl. Cancer Inst. 82 (1990) 1113-1118.

We proceeded as follows: HT-29 cells (human colon carcinoma cell line, ATCC-No. HTB-38) were cultivated in RPMI 1640 medium with GlutaMAX™ I (Invitrogen, Cat-No. 61870-010), 2.5% fetal calf serum (FCS, Sigma Cat-No. F4135 (FBS)), 2 mM glutamine, 100 units/ml penicillin, 100 μg/ml streptomycin (=Pen/Strep from Invitrogen Cat. No. 15140). For the assay the cells were seeded in 384 well plates, 900 cells per well, in the same medium. At the next day, the compounds (dissolved 10 mM in DMSO) were added in various concentrations ranging from 30 μM to 1.5 nM. After 5 days, the MTT assay was done mainly according to the instructions of the manufacturer (Cell proliferation kit I, MTT, from Roche Molecular Biochemicals). In brief: MTT labeling reagent was added to a final concentration of 0.5 mg/ml, added and incubated for 4 hrs at 37° C., 5% CO2. During this incubation time purple formazan crystals are formed. After addition of the solubilization solution (20% Sodium Dodecyl Sulfate (SDS) in 0.02 M HCl) the plates were incubated overnight at 37° C., 5% CO2. After careful mixing, the plates were measured in Victor 2 (scanning multiwell spectrophotometer, Wallac) at 550 nm.

A decrease in number of living cells results in a decrease in the total metabolic activity in the sample. The decrease directly correlates to the amount of purple colour resulting from the solubilization of the purple formazan crystals. Determination of IC90 was done using XL-fit (XLfit software (ID Business Solution Ltd., Guilford, Surrey, UK)).

The reference compound has the following structure:

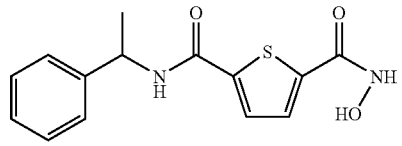

| Compounds according to this invention | IC90 HT29 [μM] |
|---|---|
| Reference compound | 1.12 |
| Example 2-14 | 0.07 |
| Example 3-1 | 0.11 |
| Examples 1-1, 3-11 | <0.10 |
| Examples 2-8, 2-1 | 0.10-0.50 |

To further demonstrate the activity of the compounds according to this invention as HDAC inhibitors, their effect on histone deacetylase inhibition was evaluated using the following biochemical quench assay:

The function of histone deacetylase (HDAC) is the deacetylation of lysines in e.g. histone H4. A peptide of 17 amino acids derived from histone H4 was labeled with tetramethylrhodamine (TAMRA, fluorophore, Invitrogen) at the C-terminus and QSY-7™ (quencher dye, Invitrogen) at the N-terminus and was used as a substrate (TAMRA-first 17 aa of histone H4-QSY7). Following deacetylation by HDAC, the enzyme Lys C is able to cleave the peptide after lysine.

This results in a loss of the quench effect and a high fluorescence signal. Inhibition of HDAC by compounds results in low signals because Lys C could not cleave the substrate and the quench effect persists.

For dose response curves, 10 concentrations were diluted 1:3 starting at 30 µM. 10 µl compound dilution were put into each well of a 384 well plate. 10 µl HDAC were added (recombinant HDAC-1 purified from HEK 293 cells (human embryonic kidney cell line transformed by Adenovirus 5 fragments, ATCC-No. CRL 1573); enzyme activity has to be assessed for each preparation). 10 µl peptide substrate was added (1 µM final concentration, derived from 1 mM stock solution diluted 1:1000 in test buffer). After 90 min incubation at room temperature, the reaction was stopped by addition of 20 µl test buffer including 3 µg/ml Lys C and 0.075% Sodium Dodecyl Sulfate (SDS). After overnight incubation the fluorescence signal of TAMRA was measured (Victor 2 from Wallac, absorption 544 nm, emission 590 nm). The O.D. of DMSO (dimethylsulfoxide)-treated control wells is 100%, the % inhibition of compound treated wells is calculated in relation to 100%. Based on 10 concentrations an IC50 curve is generated by using XLfit3 (XLfit software (ID Business Solution Ltd., Guilford, Surrey, UK)).

Test buffer used: a mixture of 10 mM 4-(2-hydroxyethyl)-1-piperazineethanesulfonic acid (HEPES) pH8, 10 mM NaCl, 10% Glycerol, 0.005% Triton X100™, 0.1 mM ethylenediaminetetraacetic acid (EDTA), 0.1 mM Tris(2-carboxyethyl)phosphine (TCEP). Used plates: 384 well plates (black, Greiner, 781077).

The reference compound has the following structure.

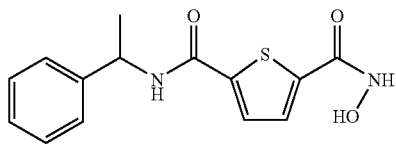

| Compounds according to this invention | IC50 HDAC quench assay [nM] |
|---|---|
| Reference compound | 3.12 |
| Example 2-8 | 2.52 |
| Example 3-12 | 4.11 |
| Examples 2-18, 4-3 | <3.00 |
| Examples 1-2, 3-9, 4-1 | 3.00-6.00 |

An embodiment of the present invention is a medicament, as defined hereinbefore, for the inhibition of tumor cell proliferation by induction of histone acetylation in said tumor cell.

Another embodiment of the present invention is a medicament, as defined hereinbefore, for the treatment of neoplasms of the hematopoetic and lymphatic system.

Still another embodiment of the present invention is a medicament, as defined hereinbefore, for the treatment of cancer.

Still another embodiment of the present invention is a medicament as defined herein before for the treatment of colon-, breast-, lung-, prostate-, rectal-, stomach-, bladder-, pancreatic- or ovarian cancer.

Yet another embodiment of the present invention is the use of one or more enantiomerically pure compounds of formula I for the manufacture of medicaments for the inhibition of tumor cell proliferation by induction of histone acetylation in said tumor cell.

Yet another embodiment of the present invention is the use of one or more enantiomerically pure compounds of formula I for the manufacture of medicaments for treatment of cancer.

Yet another embodiment of the present invention is the use of one or more enantiomerically pure compounds of formula I for the manufacture of medicaments for treatment of colon-, breast-, lung-, prostate-, rectal-, stomach-, bladder-, pancreatic- or ovarian cancer.

Yet another embodiment of the present invention is the use of one or more enantiomerically pure compounds of formula I for the manufacture of medicaments for treatment of neoplasms of the hematopoetic and lymphatic system.

Yet another embodiment of the present invention is a method for inhibiting tumor cell proliferation by induction of histone acetylation in a tumor cell, due to administering to said tumor cell an effective amount of one or more enantiomerically pure compounds of formula I. According to a further feature of this aspect of the invention there is provided a method for producing an anti-cell-proliferation effect in a warm-blooded animal, such as man, in need of such treatment which comprises administering to said animal an effective amount of an enantiomerically pure thiophene derivative as defined hereinbefore.

Therefore, still another embodiment of the present invention is the method as described above, wherein the tumor is colon-, breast-, lung-, prostate-, rectal-, stomach-, bladder-, pancreatic- or ovarian cancer.

According to a more preferred aspect of the present invention there is provided an enantiomerically pure compound of the formula I as defined hereinbefore for use in a method of treatment of the human or animal body by therapy. We have now found that the said compounds of the present invention possess anti-cell-proliferation properties which are believed to arise from their histone deacetylase inhibitory activity. Accordingly the compounds of the present invention provide a method for treating the proliferation of malignant cells. Accordingly the enantiomerically pure compounds of the present invention are expected to be useful in the treatment of cancer by providing an anti-proliferative effect, particularly in the treatment of cancers of the breast, lung, colon, rectum, stomach, prostate, bladder, pancreas and ovary. It is in addition expected that a derivative of the present invention will possess activity against a range of leukemias, lymphoid malignancies and solid tumors such as carcinomas and sarcomas in tissues such as the liver, kidney, prostate and pancreas.

The anti-cell-proliferation treatment defined hereinbefore may be applied as a sole therapy or may involve, in addition to the thiophene derivative of the invention, one or more other anti-tumor substances, for example those selected from, for example, mitotic inhibitors, for example vinblastine; alkylating agents, for example cis-platin, carboplatin and cyclophosphamide; inhibitors of microtubule assembly, like paclitaxel or other taxanes; antimetabolites, for example 5-fluorouracil, capecitabine, cytosine arabinoside and hydroxyurea, or, for example, intercalating antibiotics, for example adriamycin and bleomycin; immunostimulants, for example trastuzumab; DNA synthesis inhibitors, e.g. gemcitabine; enzymes, for example asparaginase; topoisomerase inhibitors, for example etoposide; biological response modifiers, for example interferon; and anti-hormones, for example anti-oestrogens such as tamoxifen or, for example antiandrogens such as (4'-cyano-3-(4-fluorophenylsulphonyl)-2-hydroxy-2-methyl-3'-(trifluoromethyl)-propionanilide, or other therapeutic agents and principles as described in, for example, Cancer: Principles & Practice of Oncology, Vincent T. DeVita, Jr., Samuel Hellmann, Steven A. Rosenberg; 5th ed., Lippincott-Raven Publishers, 1997. Such conjoint treatment may be achieved by way of the simultaneous, sequential or separate dosing of individual components of the treatment. According to this aspect of the invention there is provided a pharmaceutical product comprising a thiophene derivative of the formula I as defined hereinbefore and an additional anti-tumor substance as defined hereinbefore for the conjoint treatment of cancer.

The following examples and references are provided to aid the understanding of the present invention, the true scope of which is set forth in the appended claims. It is understood that modifications can be made in the procedures set forth without departing from the spirit of the invention.

EXAMPLE 1

Step 1: (R)-5-[1-(4-Bromo-phenyl)-ethylcarbamoyl]-thiophene-2-carboxylic Acid Methyl Ester To a solution of 18.64 g (0.100 mol) thiophene-2,5-dicarboxylic acid monomethyl ester in 450 ml dichloromethane, 28.76 g (0.150 mol) N'-(3-dimethylaminopropyl)-N-ethylcarbodiimid hydrochloride, 22.96 g (0.150 mol) 1-hydroxybenzotriazole hydrate and 15.21 g (0.150 mol) triethylamine were added. After 30 min at room temperature 20.00 g (0.100 mol) R-(+)-1-(4-Bromo-phenyl)-ethylamine were added. The reaction mixture was stirred for 5 h and then extracted with saturated aqueous NaHCO3 solution and with water. The organic phase was dried over MgSO4 and the solvent was evaporated. The residue was triturated with diisopropyl ether and n-heptane to provide 30.29 g (0.082 mol) (R)-5-[1-(4-Bromo-phenyl)-ethylcarbamoyl]-thiophene-2-carboxylic acid methyl ester.

Step 2: (R)-5-[1-(4-Thiophen-2-yl-phenyl)-ethylcarbamoyl]-thiophene-2-carboxylic acid methyl ester To a suspension of 0.462 g (0.0004 mol) tetrakis(triphenylphosphine)-palladium(0) in 45 ml dry dimethoxyethane, 5.00 g (0.0136 mol) (R)-5-[1-(4-bromo-phenyl)-ethylcarbamoyl]-thiophene-2-carboxylic acid methyl ester were added and stirred for 10 min at room temperature under nitrogen atmosphere. 3.65 g (0.0285 mol) thiophene-2-boronic acid in 20 ml ethanol and 14.3 ml (0.0286 mol) of a 2 M aqueous solution of Cs2CO3 were added and the mixture was heated to 75-80° C. for 3 hours. After 1.25 hours, another 0.5 equivalents of thiophene-2-boronic acid and Cs2CO3 were added to the mixture. The warm reaction mixture was filtered, the solid was washed with ethyl acetate and the solvent of the filtrates was evaporated. The residue was dissolved in dichloromethane, washed with water, dried over magnesium sulfate and the solvent was removed. The crude product was recrystallized from n-butanol/n-heptane 1:2 and dried in vacuum to give 2.52 g (0.00678 mol) (R)-5-[1-(4-thiophen-2-yl-phenyl)-ethylcarbamoyl]-thiophene-2-carboxylic acid methyl ester.

The title compound was also prepared in an analogous manner to that described in example 2, step 3 (microwave-assisted reaction).

Step 3: (R)-Thiophene-2,5-dicarboxylic acid 2-hydroxyamide 5-{[1-(4-thiophen-2-yl-phenyl)-ethyl]-amide} (compound 1-1)

To a solution of 2.52 g (0.00678 mol) (R)-5-[1-(4-thiophen-2-yl-phenyl)-ethylcarbamoyl]-thiophene-2-carboxylic acid methyl ester in 100 ml dichloromethane and 35 ml methanol, 34.1 ml (0.0682 mol) of a 2M solution of hydroxylamine in methanol and 0.430 g (0.00766 mol) potassium hydroxide in 10 ml methanol were added. After 3 h at room temperature (rt), the reaction mixture was filtered and the solid was washed with methanol. The filtrate was treated with dry ice to lower the pH value to almost neutral. Stirring was continued for 15 min and the formed precipitate was filtered off. The solid was washed with methanol and the solvent of the combined organic filtrates was evaporated. The residue was purified by preparative reversed phase chromatography. The product was then further purified by trituration with toluene and washing with diisopropylether and 1.75 g (0.0047 mol) (R)-thiophene-2,5-dicarboxylic acid 2-hydroxyamide 5-{[1-(4-thiophen-2-yl-phenyl)-ethyl]-amide} (compound 1-1) were obtained, calculated MW 372.47, found MW (M+H) 372.9; 1H-NMR (400 MHz, d6-DMSO): δ=11.35 (bs, 1H), 9.21 (bs, 1H), 8.95 (d, 1H), 7.83 (m, 1H), 7.62 (m, 2H), 7.57 (m, 1H), 7.52 (m, 1H), 7.46 (m, 1H), 7.41 (m, 2H), 7.12 (m, 1H), 5.12 (m, 1H), 1.49 (d, 3H).

In analogy to example 1-1 using the appropriate starting material, the following compounds were prepared:

| no. | name | calc. MW | found MW | 1H-NMR(400MHz; d6-DMSO) |
|---|---|---|---|---|
| 1-2 | Thiophene-2,5-dicarboxylic acid 2-{[1-(4'-dimethylamino-biphenyl-4-yl)-ethyl]-amide} 5-hydroxyamide | 409.51 | 410.1 | δ=11.34(bs, 1H), 9.22(bs, 1H), 8.94(d, 1H), 7.83(m, 1H), 7.57(m, 1H), 7.53(m, 2H), 7.48(m, 2H), 7.38(m, 2H), 6.79(m, 2H), 5.12(m, 1H), 2.92(s, 6H), 1.50(d, 3H) |
| 1-3 | Thiophene-2,5-dicarboxylic acid 2-hydroxyamide 5-{[1-(3',4',5'-trifluoro-biphenyl-4-yl)-ethyl]-amide} | 420.41 | 420.9 | δ=11.33(bs, 1H), 9.22(bs, 1H), 8.97(d, 1H), 7.83(m, 1H), 7.73-7.61(m, 4H), 7.57(m, 1H), 7.47(m, 2H), 5.15(m, 1H), 1.50(d, 3H) |
| 1-4 | Thiophene-2,5-dicarboxylic acid 2-hydroxyamide 5-{[1-(2'-methoxy-biphenyl-4-yl)- | 396.47 | 395.0(M−H) | δ=11.35(bs, 1H), 9.23(bs, 1H), 8.97(d, 1H), 7.85(m, 1H), 7.57(m, 1H), 7.41(m, 4H), 7.33(m, 1H), 7.26(m, 1H), |

-continued

| no. | name | calc. MW | found MW | 1H-NMR(400MHz; d6-DMSO) |
|---|---|---|---|---|
| | ethyl]-amide} | | | 7.09(m, 1H), 7.01(m, 1H), 5.14(m, 1H), 3.75(s, 3H), 1.52(d, 3H) |
| 1-5 | Thiophene-2,5-dicarboxylic acid 2-hydroxyamide 5-{[1-(2'-methyl-biphenyl-4-yl)-ethyl]-amide} | 380.47 9.23 | 379.0(M−H) | δ=11.35(bs, 1H), 9.23(bs, 1H), 8.98(d, 1H), 7.85(m, 1H), 7.58(m, 1H), 7.44(m, 2H), 7.35-7.14(m, 6H), 5.19(m, 1H), 2.23(s, 3H), 1.53(d, 3H) |
| 1-6 | Thiophene-2,5-dicarboxylic acid 2-{[1-(2'-fluoro-biphenyl-4-yl)-ethyl]-amide} 5-hydroxyamide | 384.43 | 385.1 | δ=11.35(bs, 1H), 9.23(bs, 1H), 8.99(d, 1H), 7.85(m, 1H), 7.58(m, 1H), 7.50(m, 5H), 7.41(m, 1H), 7.34-7.26(m, 2H), 5.16(m, 1H), 1.52(d, 3H) |
| 1-7 | Thiophene-2,5-dicarboxylic acid 2-{[1-(3'-fluoro-biphenyl-4-yl)-ethyl]-amide} 5-hydroxyamide | 384.43 | 385.1 | δ=11.35(bs, 1H), 9.23(bs, 1H), 8.98(d, 1H), 7.84(m, 1H), 7.67(m, 2H), 7.58(m, 1H), 7.53-7.43(m, 5H), 7.18(m, 1H), 5.15(m, 1H), 1.51(d, 3H) |
| 1-8 | Thiophene-2,5-dicarboxylic acid 2-hydroxyamide 5-{[1-(3'-methyl-biphenyl-4-yl)-ethyl]-amide} | 380.47 | 381.0 | δ=11.35(bs, 1H), 9.23(bs, 1H), 8.97(d, 1H), 7.84(m, 1H), 7.66-7.52(m, 3H), 7.49-7.38(m, 4H), 7.33(m, 1H), 7.16(m, 1H), 5.15(m, 1H), 2.37(s, 3H), 1.51(d, 3H) |
| 1-9 | Thiophene-2,5-dicarboxylic acid 2-hydroxyamide 5-{[1-(3'-methoxy-biphenyl-4-yl)-ethyl]-amide} | 396.47 | 397.0 | δ=11.35(bs, 1H), 9.23(bs, 1H), 8.97(d, 1H), 7.84(m, 1H), 7.62(m, 2H), 7.57(m, 1H), 7.45(m, 2H), 7.36(m, 1H), 7.20(m, 1H), 7.16(m, 1H), 6.92(m, 1H), 5.15(m, 1H), 3.81(s, 3H), 1.51(d, 3H) |
| 1-10 | Thiophene-2,5-dicarboxylic acid 2-hydroxyamide 5-({1-[4-(5-methyl-thiophen-2-yl)-phenyl]-ethyl}-amide) | 386.49 | 385.0(M−H) | δ=11.34(bs, 1H), 9.22(bs, 1H), 8.94(d, 1H), 7.83(m, 1H), 7.57(m, 1H), 7.53(m, 2H), 7.38(m, 2H), 7.25(m, 1H), 6.80(m, 1H), 5.10(m, 1H), 2.46(s, 3H), 1.48(d, 3H) |
| 1-11 | Thiophene-2,5-dicarboxylic acid 2-hydroxyamide 5-({1-[4-(1H-pyrazol-4-yl)-phenyl]-ethyl}-amide) | 356.40 | 357.1 | ν=12.90(bs, 1H), 11.34(bs, 1H), 9.23(bs, 1H), 8.92(d, 1H), 8.27-7.86(m, 2H), 7.82(m, 1H), 7.60-7.51(m, 3H), 7.34(m, 2H), 5.10(m, 1H), 1.48(d, 3H) |
| 1-12 | Thiophene-2,5-dicarboxylic acid 2-{[1-(4-cyclohexyl-phenyl)-ethyl]-amide} 5-hydroxyamide | 372.49 | 371.1(M−H) | δ=11.34(bs, 1H), 9.22(bs, 1H), 8.89(d, 1H), 7.81(m, 1H), 7.56(m, 1H), 7.27(m, 2H), 7.17(m, 2H), 5.08(m, 1H), 2.45(m, 1H), 1.82-1.16(m, 10H), 1.46(d, 3H) |

EXAMPLE 2

Step 1: 1-(3-Bromo-phenyl)-ethylamine

To a mixture of 4.97 g (0.0249 mol) 1-(3-bromo-phenyl)-ethanone and molecular sieves in 50 ml methanol, 23 g (0.298 mol) ammonium acetate and 1.75 g (0.0265 mol) sodium cyanoborohydride were added and the reaction mixture was stirred 2 d (HPLC control) at 50° C. After cooling to room temperature, the molecular sieves were filtered off and washed with methanol. The solvent of the combined filtrates was evaporated and ethyl acetate and water were added to the residue. While stirring the mixture was acidified with 6N aqueous HCl solution. The aqueous phase was separated and the organic phase was extracted two times with 1N aqueous HCl solution. Ethyl acetate was added to the combined aqueous phases and the mixture was basified with 6N NaOH. The organic phase was separated and the aqueous phase was extracted two more times with ethyl acetate. The organic combined organic phases were dried over MgSO4 and the solvent evaporated at reduced pressure to afford 2.96 g (0.0148 mol) 1-(3-bromo-phenyl)-ethylamine.

Step 2: 5-[1-(3-Bromo-phenyl)-ethylcarbamoyl]-thiophene-2-carboxylic acid methyl ester The title compound was prepared in an analogous manner to that described in example 1, step 1 from 1-(3-bromo-phenyl)-ethylamine and thiophene-2,5-dicarboxylic acid monomethyl ester.

Step 3: 5-[1-(3-Thiophen-2-yl-phenyl)-ethylcarbamoyl]-thiophene-2-carboxylic acid methyl ester The title compound was prepared in two different ways:- in a analogous manner to that described in example 1, step 2;-in a microwave-assisted reaction as described below:

To a suspension of 10.0 mg (0.0086 mmol) tetrakis(triphenylphosphine)-palladium(0) in 2 ml dry dimethoxyethane, 100 mg (0.272 mmol) 5-[1-(3-Bromo-phenyl)-ethylcarbamoyl]-thiophene-2-carboxylic acid methyl ester were added and stirred for 10 min at room temperature under nitrogen atmosphere. 52.5 mg (0.410 mmol) thiophene-2-boronic acid in 0.5 ml ethanol and 285 µl (0.570 mmol) of a 2 M aqueous solution of Na2CO3 were added and the mixture was heated in the microwave oven (Emrys Optimizer) at 100° C. for 25 min. After cooling to room temperature, the reaction mixture was filtered and the solid was washed with ethanol. The solvent of the combined filtrates was evaporated. The residue was dissolved in ethyl acetate and washed with brine. The organic phase was dried over magnesium sulfate, the solvent was evaporated and the residue was subjected to silica gel chromatography (ethyl acetate/n-heptane 1:2) to yield 81 mg (0.218 mmol) 5-[1-(3-thiophen-2-yl-phenyl)-ethylcarbamoyl]-thiophene-2-carboxylic acid methyl ester.

Step 4: Thiophene-2,5-dicarboxylic acid 2-hydroxyamide 5-{[1-(3-thiophen-2-yl-phenyl)-ethyl]-amide} (compound 2-1)

The title compound was prepared in an analogous manner to that described in example 1, step 3 from 5-[1-(3-thiophen-2-yl-phenyl)-ethylcarbamoyl]-thiophene-2-carboxylic acid methyl ester. Compound 2-1: calculated MW 372.46, found MW (M−H) 371.0; 1H-NMR (400 MHz, d6-DMSO): δ=11.34 (bs, 1H), 9.22 (bs, 1H), 8.99 (d, 1H), 7.84 (m, 1H), 7.64 (m, 1H), 7.61-7.46 (m, 4H), 7.43-7.27 (m, 2H), 7.14 (m, 1H), 5.15 (m, 1H), 1.51 (d, 3H)

In analogy to example 2-1 using the appropriate starting material, the following compounds were prepared:

| no. | name | calc. MW | found MW (M+H) | 1H-NMR(400MHz; d6-DMSO) |
| --- | --- | --- | --- | --- |
| 2-2 | Thiophene-2,5-dicarboxylic acid 2-{[1-(4'-chloro-biphenyl-3-yl)-ethyl]-amide} 5-hydroxyamide | 400.88 | 400.9 | δ=11.35(bs, 1H), 9.23(bs, 1H), 8.98(d, 1H), 7.83(m, 1H), 7.71-7.65(m, 3H), 7.60-7.50(m, 4H), 7.47-7.36(m, 2H), 5.18(m, 1H), 1.53(d, 3H) |
| 2-3 | Thiophene-2,5-dicarboxylic acid 2-hydroxyamide 5-{[1-(2'-methoxy-biphenyl-3-yl)-ethyl]-amide} | 396.46 | 397.2 | δ=11.34(bs, 1H), 9.22(bs, 1H), 8.96(d, 1H), 7.82(m, 1H), 7.56(m, 1H), 7.48(m, 1H), 7.37-7.22(m, 5H), 7.09(m, 1H), 7.02(m, 1H), 5.16(m, 1H), 3.71(s, 3H), 1.51(d, 3H) |
| 2-4 | Thiophene-2,5-dicarboxylic acid 2-hydroxyamide 5-{[1-(2'-methyl-biphenyl-3-yl)-ethyl]-amide} | 380.47 | 381.2 | δ=11.34(bs, 1H), 9.23(bs, 1H), 8.95(d, 1H), 7.81(m, 1H), 7.56(m, 1H), 7.43-7.32(m, 3H), 7.31-7.16(m, 5H), 5.18(m, 1H), 2.21(s, 3H), 1.51(d, 3H) |
| 2-5 | Thiophene-2,5-dicarboxylic acid 2-hydroxyamide 5-{[1-(4'-methoxy-biphenyl-3-yl)-ethyl]-amide} | 396.46 | 397.1 | δ=11.35(bs, 1H), 9.23(bs, 1H), 8.97(d, 1H), 7.83(m, 1H), 7.62(m, 1H), 7.60-7.54(m, 3H), 7.48(m, 1H), 7.38(m, 1H), 7.31(m, 1H), 7.03(m, 2H), 5.17(m, 1H), 3.79(s, 3H), 1.52(d, 3H) |
| 2-6 | Thiophene-2,5-dicarboxylic acid 2-{[1-(4'-dimethylamino-biphenyl-3-yl)-ethyl]-amide} 5-hydroxyamide | 409.51 | 410.0 | δ=11.34(bs, 1H), 9.23(bs, 1H), 8.96(d, 1H), 7.84(m, 1H), 7.59(m, 2H), 7.50(m, 2H), 7.45(m, 1H), 7.35(m, 1H), 7.25(m, 1H), 6.82(m, 2H), 5.16(m, 1H), 2.94(s, 6H), 1.52(d, 3H) |

-continued

| no. | name | calc. MW | found MW (M+H) | 1H-NMR(400MHz; d6-DMSO) |
|---|---|---|---|---|
| 2-7 | Thiophene-2,5-dicarboxylic acid 2-{[1-(2'-fluoro-biphenyl-3-yl)-ethyl]-amide} 5-hydroxyamide | 384.43 | 385.3 | δ=11.35(bs, 1H), 9.23(bs, 1H), 8.98(d, 1H), 7.82(m, 1H), 7.60-7.38(m, 7H), 7.35-7.27(m, 2H), 5.18(m, 1H), 1.52(d, 3H) |
| 2-8 | Thiophene-2,5-dicarboxylic acid 2-{[1-(4'-fluoro-biphenyl-3-yl)-ethyl]-amide} 5-hydroxyamide | 384.43 | 385.3 | δ=11.35(bs, 1H), 9.23(bs, 1H), 8.97(d, 1H), 7.83(m, 1H), 7.72-7.63(m, 3H), 7.57(m, 1H), 7.51(m, 1H), 7.42(m, 1H), 7.37(m, 1H), 7.30(m, 2H), 5.18(m, 1H), 1.53(d, 3H) |
| 2-9 | Thiophene-2,5-dicarboxylic acid 2-{[1-(3'-fluoro-biphenyl-3-yl)-ethyl]-amide} 5-hydroxyamide | 384.43 | 385.0 | δ=11.35(bs, 1H), 9.22(bs, 1H), 8.97(d, 1H), 7.83(m, 1H), 7.72(m, 1H), 7.62-7.36(m, 7H), 7.20(m, 1H), 5.19(m, 1H), 1.53(d, 3H) |
| 2-10 | Thiophene-2,5-dicarboxylic acid 2-hydroxyamide 5-{[1-(4'-methyl-biphenyl-3-yl)-ethyl]-amide} | 380.47 | 381.0 | δ=11.35(bs, 1H), 9.23(bs, 1H), 8.98(d, 1H), 7.83(m, 1H), 7.65(m, 1H), 7.61-7.47(m, 4H), 7.40(m, 1H), 7.34(m, 1H), 7.28(m, 2H), 5.18(m, 1H), 2.34(s, 3H), 1.53(d, 3H) |
| 2-11 | Thiophene-2,5-dicarboxylic acid 2-{[1-(2'-chloro-biphenyl-3-yl)-ethyl]-amide} 5-hydroxyamide | 400.88 | 401.1 | δ=11.34(bs, 1H), 9.23(bs, 1H), 8.98(d, 1H), 7.82(m, 1H), 7.59-7.53(m, 2H), 7.48-7.37(m, 6H), 7.31(m, 1H), 5.18(m, 1H), 1.52(d, 3H) |
| 2-12 | Thiophene-2,5-dicarboxylic acid 2-{[1-(3'-chloro-biphenyl-3-yl)-ethyl]-amide} 5-hydroxyamide | 400.88 | 401.1 | δ=11.32(bs, 1H), 9.23(bs, 1H), 8.97(d, 1H), 7.82(m, 1H), 7.75-7.67(m, 2H), 7.65-7.36(m, 7H), 5.16(m, 1H), 1.52(d, 3H) |
| 2-13 | Thiophene-2,5-dicarboxylic acid 2-hydroxyamide 5-{[1-(3'-methyl-biphenyl-3-yl)-ethyl]-amide} | 380.47 | 381.5 | δ=11.34(bs, 1H), 9.22(bs, 1H), 8.98(d, 1H), 7.83(m, 1H), 7.65(m, 1H), 7.61-7.31(m, 7H), 7.18(m, 1H), 5.18(m, 1H), 2.38(s, 3H), 1.53(d, 3H) |
| 2-14 | Thiophene-2,5-dicarboxylic acid 2-{[1-(3-benzo[b]thiophen-2-yl-phenyl)-ethyl]-amide} 5-hydroxyamide | 422.53 | 423.0 | δ=11.36(bs, 1H), 9.24(bs, 1H), 9.03(d, 1H), 7.98(m, 1H), 7.89-7.82(m, 3H), 7.79(m, 1H), 7.67(m, 1H), 7.58(m, 1H), 7.49-7.32(m, 4H), 5.19(m, 1H), 1.54(d, 3H) |
| 2-15 | Thiophene-2,5-dicarboxylic acid 2-hydroxyamide 5-{[1-(3'-methoxy-biphenyl-3-yl)-ethyl]-amide} | 396.46 | 397.0 | δ=11.34(bs, 1H), 9.23(bs, 1H), 8.98(d, 1H), 7.83(m, 1H), 7.66(m, 1H), 7.57(m, 1H), 7.53(m, 1H), 7.45-7.34(m, 3H), 7.21(m, 1H), 7.16(m, 1H), 6.94(m, 1H), 5.19(m, 1H), 3.82(s, 3H), 1.53(d, 3H) |
| 2-16 | Thiophene-2,5-dicarboxylic acid 2-hydroxyamide 5- | 444.53 | 445.3 | δ=11.35(bs, 1H), 9.23(bs, 1H), 9.00(d, 1H), 8.01(m, 2H), |

| no. | name | calc. MW | found MW (M+H) | 1H-NMR(400MHz; d6-DMSO) |
|---|---|---|---|---|
| | {[1-(4'-methanesulfonyl-biphenyl-3-yl)-ethyl]-amide} | | | 7.92(m, 2H), 7.83(m, 1H), 7.76(m, 1H), 7.63(m, 1H), 7.57(m, 1H), 7.53-7.42(m, 2H), 5.21(m, 1H), 3.25(s, 3H), 1.54(d, 3H) |
| 2-17 | Thiophene-2,5-dicarboxylic acid 2-hydroxyamide 5-({1-[3-(5-methyl-thiophen-2-yl)-phenyl]-ethyl}-amide) | 386.49 | 387.1 | δ=11.31(bs, 1H), 9.24(bs, 1H), 8.98(d, 1H), 7.83(m, 1H), 7.60-7.52(m, 2H), 7.45(m, 1H), 7.35(m, 1H), 7.30-7.25(m, 2H), 6.82(m, 1H), 5.13(m, 1H), 2.46(s, 3H), 1.50(d, 3H) |
| 2-18 | Thiophene-2,5-dicarboxylic acid 2-hydroxyamide 5-({1-[3-(1H-pyrazol-4-yl)-phenyl]-ethyl}-amide) | 356.40 | 357.2 | δ=12.93(bs, 1H), 11.34(bs, 1H), 9.22(bs, 1H), 8.93(d, 1H), 8.32-7.87(m, 2H), 7.84(m, 1H), 7.58(m, 2H), 7.47(m, 1H), 7.31(m, 1H), 7.20(m, 1H), 5.13(m, 1H), 1.51(d, 3H) |
| 2-19 | Thiophene-2,5-dicarboxylic acid 2-({1-[3-(3,5-dimethyl-isoxazol-4-yl)-phenyl]-ethyl}-amide) 5-hydroxyamide | 385.44 | 385.8 | δ=11.35(bs, 1H), 9.23(bs, 1H), 8.97(d, 1H), 7.82(m, 1H), 7.57(m, 1H), 7.43(m, 1H), 7.40-7.35(m, 2H), 7.26(m, 1H), 5.16(m, 1H), 2.39(s, 3H), 2.22(s, 3H), 1.51(d, 3H) |
| 2-20 | Thiophene-2,5-dicarboxylic acid 2-hydroxyamide 5-({1-[3-(1H-indol-5-yl)-phenyl]-ethyl}-amide) | 405.48 | 406.1 | δ=11.14(bs, 1H), 9.24(bs, 1H), 8.99(d, 1H), 7.87-7.76(m, 2H), 7.68(m, 1H), 7.62-7.28(m, 7H), 6.49(m, 1H), 5.19(m, 1H), 1.54(d, 3H) |
| 2-21 | Thiophene-2,5-dicarboxylic acid 2-hydroxyamide 5-{[1-(3-pyridin-3-yl-phenyl)-ethyl]-amide} | 367.43 | 368.1 | δ=11.35(bs, 1H), 9.23(bs, 1H), 8.98(d, 1H), 8.88(m, 1H), 8.58(m, 1H), 8.06(m, 1H), 7.84(m, 1H), 7.74(m, 1H), 7.63-7.55(m, 2H), 7.52-7.40(m, 3H), 5.20(m, 1H), 1.54(d, 3H) |

EXAMPLE 3

Step 1: 1-(5-Bromo-thiophen-2-yl)-ethylamine

The title compound was prepared in an analogous manner to that described in example 2, step 1 from 1-(5-bromo-thiophen-2-yl)-ethanone.

Step 2: 5-[1-(5-Bromo-thiophen-2-yl)-ethylcarbamoyl]-thiophene-2-carboxylic acid methyl ester The title compound was prepared in an analogous manner to that described in example 1, step 1 from 1-(5-bromo-thiophen-2-yl)-ethylamine and thiophene-2,5-dicarboxylic acid monomethyl ester.

Step 3: 5-{1-[5-(2-Methoxy-phenyl)-thiophen-2-yl]-ethylcarbamoyl}-thiophene-2-carboxylic acid methyl ester The title compound was prepared in an analogous manner to that described in example 2, step 3 from 5-[1-(5-bromo-thiophen-2-yl)-ethylcarbamoyl]-thiophene-2-carboxylic acid methyl ester and 2-methoxy-benzene-boronic acid.

Step 4: Thiophene-2,5-dicarboxylic acid 2-hydroxyamide 5-({1-[5-(2-methoxy-phenyl)-thiophen-2-yl]-ethyl}-amide) (compound 3-1)

The title compound was prepared in an analogous manner to that described in example 1, step 3 from 5-{1-[5-(2-methoxy-phenyl)-thiophen-2-yl]-ethylcarbamoyl}-thiophene-2-carboxylic acid methyl ester. Compound 3-1: calculated MW 402.49, found MW (M+Na) 425.12; 1H-NMR (400 MHz, d6-DMSO): δ=11.36 (bs, 1H), 9.24 (bs, 1H), 9.08 (d, 1H), 7.80 (m, 1H), 7.65 (m, 1H), 7.57 (m, 1H), 7.41 (m, 1H), 7.27 (m, 1H), 7.12 (m, 1H), 7.02-6.95 (m, 2H), 5.38 (m, 1H), 3.87 (s, 3H), 1.60 (d, 3H).

In analogy to example 3-1 using the appropriate starting material, the following compounds were prepared:

| no. | name | calc. MW | found MW (M+H) | 1H-NMR(400MHz; d6-DMSO) |
|---|---|---|---|---|
| 3-2 | Thiophene-2,5-dicarboxylic acid 2-({1-[5-(4-dimethylamino-phenyl)-thiophen-2-yl]-ethyl}-amide) 5-hydroxyamide | 415.54 | 415.7 | δ=11.36(bs, 1H), 9.24(bs, 1H), 9.05(d, 1H), 7.79(m, 1H), 7.57(m, 1H), 7.40(m, 2H), 7.10(m, 1H), 6.93(m, 1H), 6.72(m, 2H), 5.34(m, 1H), 2.91(m, 6H), 1.58(d, 3H) |
| 3-3 | Thiophene-2,5-dicarboxylic acid 2-hydroxyamide 5-{[1-(5-o-tolyl-thiophen-2-yl)-ethyl]-amide} | 386.49 | 387.2 | δ=11.35(bs, 1H), 9.24(bs, 1H), 9.11(d, 1H), 7.80(m, 1H), 7.56(m, 1H), 7.37-7.19(m, 4H), 7.06-7.03(m, 2H), 5.40(m, 1H), 2.38(s, 3H), 1.61(d, 3H) |
| 3-4 | Thiophene-2,5-dicarboxylic acid 2-hydroxyamide 5-{[1-(5-m-tolyl-thiophen-2-yl)-ethyl]-amide} | 386.49 | 386.8 | δ=11.36(bs, 1H), 9.24(bs, 1H), 9.10(d, 1H), 7.80(m, 1H), 7.57(m, 1H), 7.43-7.37(m, 2H), 7.33(m, 1H), 7.27(m, 1H), 7.09(m, 1H), 7.01(m, 1H), 5.36(m, 1H), 2.32(s, 3H), 1.60(d, 3H) |
| 3-5 | Thiophene-2,5-dicarboxylic acid 2-hydroxyamide 5-{[1-(5-p-tolyl-thiophen-2-yl)-ethyl]-amide} | 386.49 | 387.2 | δ=11.36(bs, 1H), 9.24(bs, 1H), 9.09(d, 1H), 7.80(m, 1H), 7.57(m, 1H), 7.48(m, 2H), 7.29(m, 1H), 7.19(m, 2H), 6.99(m, 2H), 5.36(m, 1H), 2.30(s, 3H), 1.59(d, 3H) |
| 3-6 | Thiophene-2,5-dicarboxylic acid 2-({1-[5-(2-chloro-phenyl)-thiophen-2-yl]-ethyl}-amide) 5-hydroxyamide | 406.91 | 407.2 | δ=11.36(bs, 1H), 9.24(bs, 1H), 9.13(d, 1H), 7.80(m, 1H), 7.63-7.52(m, 3H), 7.43-7.31(m, 2H), 7.30(m, 1H), 7.07(m, 1H), 5.41(m, 1H), 1.62(d, 3H) |
| 3-7 | Thiophene-2,5-dicarboxylic acid 2-hydroxyamide 5-({1-[5-(4-methoxy-phenyl)-thiophen-2-yl]-ethyl}-amide) | 402.49 | 403.0 | δ=11.41(bs, 1H), 9.26(bs, 1H), 9.08(d, 1H), 7.80(m, 1H), 7.54-7.50(m, 3H), 7.20(m, 1H), 7.02-6.91(m, 3H), 5.35(m, 1H), 3.76(s, 3H), 1.59(d, 3H) |
| 3-8 | Thiophene-2,5-dicarboxylic acid 2-({1-[5-(4-fluoro-phenyl)-thiophen-2-yl]-ethyl}-amide) 5-hydroxyamide | 390.46 | 391.0 | δ=11.36(bs, 1H), 9.24(bs, 1H), 9.10(d, 1H), 7.79(m, 1H), 7.63(m, 2H), 7.57(m, 1H), 7.32(m, 1H), 7.22(m, 2H), 7.01(m, 1H), 5.36(m, 1H), 1.60(d, 3H) |
| 3-9 | Thiophene-2,5-dicarboxylic acid 2-({1-[5-(3-fluoro- | 390.46 | 391.2 | δ=11.35(bs, 1H), 9.24(bs, 1H), 9.11(d, 1H), 7.80(m, |

| no. | name | calc. MW | found MW (M+H) | 1H-NMR(400MHz; d6-DMSO) |
|---|---|---|---|---|
| | phenyl)-thiophen-2-yl]-ethyl}-amide) 5-hydroxyamide | | | 1H), 7.57(m, 1H), 7.50-7.36(m, 4H), 7.10(m, 1H), 7.04(m, 1H), 5.38(m, 1H), 1.60(d, 3H) |
| 3-10 | Thiophene-2,5-dicarboxylic acid 2-({1-[5-(4-chloro-phenyl)-thiophen-2-yl]-ethyl}-amide) 5-hydroxyamide | 406.91 | 407.0 | δ=11.35(bs, 1H), 9.24(bs, 1H), 9.10(d, 1H), 7.80(m, 1H), 7.63(m, 2H), 7.56(m, 1H), 7.43(m, 2H), 7.40(m, 1H), 7.03(m, 1H), 5.37(m, 1H), 1.60(d, 3H) |
| 3-11 | Thiophene-2,5-dicarboxylic acid 2-({1-[5-(3-chloro-phenyl)-thiophen-2-yl]-ethyl}-amide) 5-hydroxyamide | 406.91 | 429.03(M+Na) | δ=11.37(bs, 1H), 9.24(bs, 1H), 9.12(d, 1H), 7.80(m, 1H), 7.68(m, 1H), 7.60-7.52(m, 2H), 7.48(m, 1H), 7.41(m, 1H), 7.33(m, 1H), 7.05(m, 1H), 5.38(m, 1H), 1.60(d, 3H) |
| 3-12 | Thiophene-2,5-dicarboxylic acid 2-({1-[5-(2-fluoro-phenyl)-thiophen-2-yl]-ethyl}-amide) 5-hydroxyamide | 390.46 | 391.1 | δ=11.37(bs, 1H), 9.24(bs, 1H), 9.12(d, 1H), 7.80(m, 1H), 7.73(m, 1H), 7.57(m, 1H), 7.43(m, 1H), 7.38-7.20(m, 3H), 7.08(m, 1H), 5.40(m, 1H), 1.61(d, 3H) |
| 3-13 | Thiophene-2,5-dicarboxylic acid 2-hydroxyamide 5-({1-[5-(3-methoxy-phenyl)-thiophen-2-yl]-ethyl}-amide) | 402.49 | 425.05(M+Na) | δ=11.35(bs, 1H), 9.24(bs, 1H), 9.09(d, 1H), 7.80(m, 1H), 7.56(m, 1H), 7.38(m, 1H), 7.30(m, 1H), 7.16(m, 1H), 7.12(m, 1H), 7.02(m, 1H), 6.86(m, 1H), 5.37(m, 1H), 3.79(s, 3H), 1.60(d, 3H) |
| 3-14 | Thiophene-2,5-dicarboxylic acid 2-hydroxyamide 5-({1-[5-(4-methanesulfonyl-phenyl)-thiophen-2-yl]-ethyl}-amide) | 450.56 | 450.7 | δ=11.37(bs, 1H), 9.25(bs, 1H), 9.15(d, 1H), 7.95-7.84(m, 4H), 7.81(m, 1H), 7.59(m, 2H), 7.10(m, 1H), 5.40(m, 1H), 3.22(s, 3H), 1.61(d, 3H) |
| 3-15 | Thiophene-2,5-dicarboxylic acid 2-{[1-(5-benzo[b]thiophen-2-yl-thiophen-2-yl)-ethyl]-amide} 5-hydroxyamide | 428.55 | 426.9(M−H) | δ=11.37(bs, 1H), 9.25(bs, 1H), 9.14(d, 1H), 7.92(m, 1H), 7.86-7.76(m, 2H), 7.61-7.52(m, 2H), 7.41-7.27(m, 3H), 7.04(m, 1H), 5.38(m, 1H), 1.61(d, 3H) |
| 3-16 | Thiophene-2,5-dicarboxylic acid 2-({1-[5-(3,5-dimethyl-isoxazol-4-yl)-thiophen-2-yl]-ethyl}-amide) 5-hydroxyamide | 391.47 | 392.0 | δ=11.36(bs, 1H), 9.24(bs, 1H), 9.11(d, 1H), 7.79(m, 1H), 7.56(m, 1H), 7.10-7.03(m, 2H), 5.39(m, 1H), 2.46(s, 3H), 2.28(s, 3H), 1.60(d, 3H) |
| 3-17 | Thiophene-2,5-dicarboxylic acid 2-hydroxyamide 5-({1-[5-(1H-indol-5-yl)-thiophen-2-yl]-ethyl}-amide) | 411.50 | 434.03(M+Na) | δ=11.35(bs, 1H), 11.15(bs, 1H), 9.24(bs, 1H), 9.09(d, 1H), 7.81(m, 1H), 7.75(m, 1H), 7.57(m, 1H), 7.42-7.29(m, 3H), 7.22(m, |

-continued

| no. | name | calc. MW | found MW (M+H) | 1H-NMR(400MHz; d6-DMSO) |
|---|---|---|---|---|
| 3-18 | Thiophene-2,5-dicarboxylic acid 2-hydroxyamide 5-{[1-(5-pyridin-3-yl-thiophen-2-yl)-ethyl]-amide} | 373.46 | 374.0 | 1H), 6.98(m, 1H), 6.43(m, 1H), 5.37(m, 1H), 1.61(d, 3H) δ=11.37(bs, 1H), 9.24(bs, 1H), 9.13(d, 1H), 8.85(m, 1H), 8.47(m, 1H), 7.99(m, 1H), 7.81(m, 1H), 7.57(m, 1H), 7.50(m, 1H), 7.44-7.38(m, 1H), 7.08(m, 1H), 5.39(m, 1H), 1.61(d, 3H) |

EXAMPLE 4

(R)-Thiophene-2,5-dicarboxylic acid 2-hydroxyamide 5-{[1-(4-morpholin-4-yl-phenyl)-ethyl]-amide}(compound 4-1) was prepared in two different ways.

EXAMPLE 4a

Via a Buchwald-Hartwig Coupling of Enantiomerically Pure (R)-5-[1-(4-bromo-phenyl)-ethylcarbamoyl]-thiophene-2-carboxylic acid methyl ester with Morpholine

EXAMPLE 4b

Via a Reductive Amination of Commercially Available 1-(4-morpholin-4-yl-phenyl)-ethanone and Via Separation of Enantiomers by Chiral HPLC

EXAMPLE 4a

Step 1: (R)-5-[1-(4-Morpholin-4-yl-phenyl)-ethylcarbamoyl]-thiophene-2-carboxylic acid methyl ester To a suspension of 1.0 mg (0.0045 mmol) palladium(II) acetate, 4.06 mg (0.0065 mmol) 2,2'-bis-(diphenylphosphino)-1,1'-binaphtyl (BINAP) and 125 mg (0.384 mmol) cesium carbonate in 1 ml dry toluene, 100 mg (0.272 mmol) (R)-5-[1-(4-Bromo-phenyl)-ethylcarbamoyl]-thiophene-2-carboxylic acid methyl ester (see example 1, step 1) and 30.0 mg (0.344 mmol) morpholine were added under an argon atmosphere. The mixture was heated in the microwave oven (Emrys Optimizer) at 160° C. for 15 min. After cooling to room temperature, the reaction mixture was filtered and the solid was washed with toluene. The solvent of the combined filtrates was evaporated and the crude product purified by preparative HPLC to yield 7.9 mg (0.021 mmol) (R)-5-[1-(4-Morpholin-4-yl-phenyl)-ethylcarbamoyl]-thiophene-2-carboxylic acid methyl ester.

Step 2: (R)-Thiophene-2,5-dicarboxylic acid 2-hydroxyamide 5-{[1-(4-morpholin-4-yl-phenyl)-ethyl]-amide} (compound 4-1)

The title compound was prepared in an analogous manner to that described in example 1, step 3 from (R)-5-[1-(4-Morpholin-4-yl-phenyl)-ethylcarbamoyl]-thiophene-2-carboxylic acid methyl ester. Compound 4-1: calculated MW 375.45, found MW (M+H) 376.0; 1H-NMR (400 MHz, d6-DMSO): δ=11.33 (bs, 1H), 9.22 (bs, 1H), 8.82 (d, 1H), 7.80 (m, 1H), 7.55 (m, 1H), 7.23 (m, 2H), 6.90 (m, 2H), 5.04 (m, 1H), 3.72 (m, 4H), 3.05 (m, 4H), 1.44 (d, 3H).

EXAMPLE 4b

Step 1: 1-(4-Morpholin-4-yl-phenyl)-ethylamine

Goddard, C. J., et al., J. Heterocycl. Chem. 28 (1991) 17

Step 2: 5-[1-(4-Morpholin-4-yl-phenyl)-ethylcarbamoyl]-thiophene-2-carboxylic acid methyl ester The title compound was prepared in an analogous manner to that described in example 1, step 1 from 1-(4-Morpholin-4-yl-phenyl)-ethylamine and thiophene-2,5-dicarboxylic acid monomethyl ester.

Step 3: (R)-5-[1-(4-Morpholin-4-yl-phenyl)-ethylcarbamoyl]-thiophene-2-carboxylic acid methyl ester The racemic 5-[1-(4-morpholin-4-yl-phenyl)-ethylcarbamoyl]-thiophene-2-carboxylic acid methyl ester was separated into both enantiomers by chiral HPLC employing a Chiralpak AD column, Daicel Chemical Industries Ltd. (eluent hexane/ethanol 80:20).

Step 4: (R)-Thiophene-2,5-dicarboxylic acid 2-hydroxyamide 5-{[1-(4-morpholin-4-yl-phenyl)-ethyl]-amide} (compound 4-1)

The title compound was prepared analogous to example 4a, step 2.

In analogy to example 4-1 using the appropriate starting material, the following compounds were prepared:

| no. | name | calc. MW | found MW (M+H) | 1H-NMR(400MHz; d6-DMSO) |
|---|---|---|---|---|
| 4-2 | Thiophene-2,5-dicarboxylic acid 2-hydroxyamide 5-{[1-(4-imidazol-1-yl- | 356.40 | 357.0 | δ=11.31(bs, 1H), 9.18(bs, 1H), 8.95(d, 1H), 8.20(s, 1H), 7.81(m, 1H), 7.70(m, 1H), 7.60(m, 2H), |

-continued

| no. | name | calc. MW | found MW (M+H) | 1H-NMR(400MHz; d6-DMSO) |
|---|---|---|---|---|
| | phenyl)-ethyl]-amide} | | | 7.56-7.46(m, 3H), 7.09(m, 1H), 5.15(m, 1H), 1.50(d, 3H) |
| 4-3 | Thiophene-2,5-dicarboxylic acid 2-hydroxyamide 5-{[1-(4-piperidin-1-yl-phenyl)-ethyl]-amide} | 373.48 | 374.2 | δ=11.34(bs, 1H), 9.23(bs, 1H), 8.81(d, 1H), 7.79(m, 1H), 7.55(m, 1H), 7.19(m, 2H), 6.87(m, 2H), 5.03(m, 1H), 3.08(t, 4H), 1.59(m, 4H), 1.51(m, 2H), 1.44(d, 3H) |
| 4-4 | Thiophene-2,5-dicarboxylic acid 2-hydroxyamide 5-({1-[4-(4-methyl-piperazin-1-yl)-phenyl]-ethyl}-amide); compound with acetic acid | 388.49 | 389.0 | δ=11.34(bs, 1H), 9.23(bs, 1H), 8.82(d, 1H), 7.79(m, 1H), 7.55(m, 1H), 7.22(m, 2H), 6.90(m, 2H), 5.03(m, 1H), 3.13(m, 4H), 2.59(m, 4H), 2.32(s, 3H), 1.44(d, 3H) |

EXAMPLE 5

Step 1: 3-Oxo-3-(3-trifluoromethyl-phenyl)-propionic acid ethyl ester

A mixture of 1.96 g (0.0275 mol) sodium ethoxide (95%) and 22 ml ethanol was stirred 20 minutes at room temperature and was then cooled with an ice bath. 3.65 g (0.025 mol) diethyloxalate followed by 4.7 g (0.025 mol) 1-(3-trifluoromethyl-phenyl)-ethanone were added slowly. The mixture was stirred for 30 min. at 0-5° C., then allowed to warm to room temperature and additional 25 ml ethanol were added. After 1 d at room temperature the solvent was evaporated. Water and diethylether were added to the residue. The organic phase was separated and the aqueous phase was extracted one more time with diethyl ether. The aqueous phase was acidified with 2M HCl to pH2 and extracted three times with diethyl ether. The combined organic phases were dried over magnesium sulfate, the solvent was evaporated and the residue triturated with petrol ether to give 5.35 g (0.0185 mol) 3-oxo-3-(3-trifluoromethyl-phenyl)-propionic acid ethyl ester.

Step 2: 5-(3-Trifluoromethyl-phenyl)-isoxazole-3-carboxylic acid ethyl ester A mixture of 5.35 g (0.0185 mol) 3-oxo-3-(3-trifluoromethyl-phenyl)-propionic acid ethyl ester and 3.87 g (0.056 mol) hydroxylamine hydrochloride in 45 ml ethanol was heated under reflux for 2 h. While cooling to room temperature, a white solid precipitated which was filtered off. The filtrate was concentrated in vacuo, diluted with 50 ml water and extracted three times with diethyl ether. The combined ethereal extracts were washed with brine, and 1N aqueous NaOH and dried over magnesium sulfate. The solvent was evaporated and toluene was added to the residue. The insoluble solid was filtered off, washed with toluene and the solvent of the combined filtrates was evaporated to yield 2.06 g (0.00723 mol) 5-(3-trifluoromethyl-phenyl)-isoxazole-3-carboxylic acid ethyl ester.

Step 3: 1-[5-(3-Trifluoromethyl-phenyl)-isoxazol-3-yl]-ethanone

To a cooled (5-10° C.) solution of 4.6 ml (0.014 mol) methyl magnesium iodide solution (3M in diethyl ether) and 5.8 ml (0.042 mol) triethylamine in 10 ml toluene, a solution of 2.06 g (0.00723 mol) 5-(3-trifluoromethyl-phenyl)-isoxazole-3-carboxylic acid ethyl ester in 20 ml toluene was added dropwise. After the addition was complete, the reaction mixture was stirred at 0-5° C. for 2 h and then treated with 5.6 ml 4N aqueous HCl solution. The mixture was filtered over celite. The aqueous phase was separated and the organic layer was washed with water, 5% aqueous NaHCO3 solution and twice with water. The organic phase was dried over magnesium sulfate and the solvent was evaporated. The residue was dissolved in a mixture of 28 ml MeOH and 0.45 ml 20% aqueous KOH solution. The solution was heated to 45° C. for 30 min, then cooled and acidified to pH 2 by addition of 6N HCl. The solvent was evaporated and the residue was mixed with toluene and aqueous NaHCO3 solution. The mixture was filtered over celite. The organic layer was separated and the solvent was evaporated to yield 0.7 g (0.00274 mol) 1-[5-(3-trifluoromethyl-phenyl)-isoxazol-3-yl]-ethanone.

Step 4: 1-[5-(3-Trifluoromethyl-phenyl)-isoxazol-3-yl]-ethylamine

The title compound was prepared in analogous manner to those described in example 2, step 1

Step 5: 5-{1-[5-(3-Trifluoromethyl-phenyl)-isoxazol-3-yl]-ethylcarbamoyl}-thiophene-2-carboxylic acid methyl ester The title compound was prepared in analogous manner to those described in example 1, step 1

Step 6: Thiophene-2,5-dicarboxylic acid 2-hydroxyamide 5-({1-[5-(3-trifluoromethyl-phenyl)-isoxazol-3-yl]-ethyl}-amide) (compound 5-1)

The title compound was prepared in analogous manner to those described in example 1, step 3.

Compound 5-1: calculated MW 425.39, found MW (M+H) 426.0; 1H-NMR (400 MHz, d6-DMSO): δ=11.37 (bs, 1H), 9.23 (bs, 1H), 9.11 (d, 1H), 8.22 (s, 1H), 8.18 (m, 1H), 7.90-7.74 (m, 3H), 7.57 (m, 1H), 7.26 (s, 1H), 5.31 (m, 1H), 1.59 (d, 3H).

In analogy to example 5-1 using the appropriate starting material the following compounds were prepared:

| no. | name | calc. MW | found MW (M+H) | 1H-NMR(400MHz; d6-DMSO) |
|---|---|---|---|---|
| 5-2 | Thiophene-2,5-dicarboxylic acid 2-hydroxyamide 5-({1-[5-(4-trifluoromethyl-phenyl)-isoxazol-3-yl]-ethyl}-amide) | 425.39 | 426.0 | 11.37(bs, 1H), 9.24(bs, 1H), 9.11(d, 1H), 8.10(m, 2H), 7.90(m, 2H), 7.81(m, 1H), 7.57(m, 1H), 7.21(s, 1H), 5.31(m, 1H), 1.59(d, 3H) |

LIST OF REFERENCES

Baraldi, P. G., et al., J. Heterocyclic Chem. 19 (1982) 557-560
Bastin, R. J., et al., Organic Proc. Res. Dev. 4 (2000) 427-435

The invention claimed is:

1. The (R)-enantiomers, (S)-enantiomers, or racemates of the compounds of formula I:

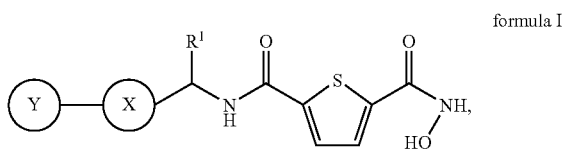

wherein:
(a) $R^1$ is a $(C_1$-$C_6)$alkyl, which is optionally substituted one or more times by halogen;
(b) X is phenylene or heteroarylene; and
(c) Y is selected from the group consisting of:
  (1) a saturated $(C_3$-$C_7)$carbocyclic group;
  (2) a saturated heterocyclic group;
  (3) a heteroaryl group; and
  (4) a phenyl group, which is substituted one to three times by alkyl, halogen, —O-alkyl, —S(O)$_2$-alkyl, —NH(alkyl) or —N(alkyl)$_2$; wherein the alkyl groups are optionally substituted with one or more halogen atoms;

and all pharmaceutically acceptable salts thereof.

2. The compounds of claim 1, wherein X is phenylene, thiophenediyl, or isoxazolediyl.

3. The compounds of claim 1 wherein X is phenylene.

4. The compounds of claim 1, wherein X is thiophenediyl.

5. The compounds of claim 1 wherein Y is a phenyl group, which is substituted one to three times by alkyl, halogen, —O-alkyl, —S(O)$_2$-alkyl, —NH(alkyl) or —N(alkyl)$_2$; wherein the alkyl groups are optionally substituted with one or more halogen atoms.

6. The compounds of claim 1 wherein Y is a heteroaryl group.

7. A compound of claim 1 selected from the group consisting of:
   Thiophene-2,5-dicarboxylic acid 2-hydroxyamide 5-({1-[5-(2-methoxy-phenyl)-thiophen-2-yl]-ethyl}-amide);
   Thiophene-2,5-dicarboxylic acid 2-({1-[5-(4-dimethylamino-phenyl)-thiophen-2-yl]-ethyl}-amide) 5-hydroxyamide;
   Thiophene-2,5-dicarboxylic acid 2-hydroxyamide 5-{[1-(5-o-tolyl-thiophen-2-yl)-ethyl]-amide};
   Thiophene-2,5-dicarboxylic acid 2-hydroxyamide 5-{[1-(5-m-tolyl-thiophen-2-yl)-ethyl]-amide}; and
   Thiophene-2,5-dicarboxylic acid 2-hydroxyamide 5-{[1-(5-p-tolyl-thiophen-2-yl)-ethyl]-amide}.

8. A compound of claim 1 selected from the group consisting of:
   Thiophene-2,5-dicarboxylic acid 2-({1-[5-(2-chloro-phenyl)-thiophen-2-yl]-ethyl}-amide) 5-hydroxyamide;
   Thiophene-2,5-dicarboxylic acid 2-hydroxyamide 5-({1-[5-(4-methoxy-phenyl)-thiophen-2-yl]-ethyl}-amide);
   Thiophene-2,5-dicarboxylic acid 2-({1-[5-(4-fluoro-phenyl)-thiophen-2-yl]-ethyl}-amide) 5-hydroxyamide;
   Thiophene-2,5-dicarboxylic acid 2-({1-[5-(3-fluoro-phenyl)-thiophen-2-yl]-ethyl}-amide) 5-hydroxyamide; and
   Thiophene-2,5-dicarboxylic acid 2-({1-[5-(4-chloro-phenyl)-thiophen-2-yl]-ethyl}-amide) 5-hydroxyamide.

9. A compound of claim 1 selected from the group consisting of:
   Thiophene-2,5-dicarboxylic acid 2-({1-[5-(3-chloro-phenyl)-thiophen-2-yl]-ethyl}-amide) 5-hydroxyamide;

Thiophene-2,5-dicarboxylic acid 2-({1-[5-(2-fluoro-phenyl)-thiophen-2-yl]-ethyl}-amide) 5-hydroxyamide;

Thiophene-2,5-dicarboxylic acid 2-hydroxyamide 5-({1-[5-(3-methoxy-phenyl)-thiophen-2-yl]-ethyl}-amide); and Thiophene-2,5-dicarboxylic acid 2-hydroxyamide 5-({1-[5-(4-methanesulfonyl-phenyl)-thiophen-2-yl]-ethyl}-amide).

10. A compound of claim 1 selected from the group consisting of:

Thiophene-2,5-dicarboxylic acid 2-{[1-(5-benzo[b]thiophen-2-yl-thiophen-2-yl)-ethyl]-amide} 5-hydroxyamide;

Thiophene-2,5-dicarboxylic acid 2-({1-[5-(3,5-dimethyl-isoxazol-4-yl)-thiophen-2-yl]-ethyl}-amide)5-hydroxyamide;

Thiophene-2,5-dicarboxylic acid 2-hydroxyamide 5-({1-[5-(1H-indol-5-yl)-thiophen-2-yl]-ethyl}-amide);

Thiophene-2,5-dicarboxylic acid 2-hydroxyamide 5-{[1-(5-pyridin-3-yl-thiophen-2-yl)-ethyl]-amide}; and Thiophene-2,5-dicarboxylic acid 2-{[1-(4'-dimethylamino-biphenyl-4-yl)-ethyl]-amide}5-hydroxyamide.

11. A compound of claim 1 selected from the group consisting of:

(R)-Thiophene-2,5-dicarboxylic acid 2-hydroxyamide 5-{[1-(3',4',5'-trifluoro-biphenyl-4-yl)-ethyl]-amide};

(R)-Thiophene-2,5-dicarboxylic acid 2-hydroxyamide 5-{[1-(2'-methoxy-biphenyl-4-yl)-ethyl]-amide};

(R)-Thiophene-2,5-dicarboxylic acid 2-hydroxyamide 5-{[1-(2'-methyl-biphenyl-4-yl)-ethyl]-amide};

(R)-Thiophene-2,5-dicarboxylic acid 2-{[1-(2'-fluoro-biphenyl-4-yl)-ethyl]-amide} 5-hydroxyamide;

(R)-Thiophene-2,5-dicarboxylic acid 2-{[1-(3'-fluoro-biphenyl-4-yl)-ethyl]-amide} 5-hydroxyamide;

(R)-Thiophene-2,5-dicarboxylic acid 2-hydroxyamide 5-{[1-(3'-methyl-biphenyl-4-yl)-ethyl]-amide}; and (R)-Thiophene-2,5-dicarboxylic acid 2-hydroxyamide 5-{[1-(3'-methoxy-biphenyl-4-yl)-ethyl]-amide}.

12. A compound of claim 1 selected from the group consisting of:

Thiophene-2,5-dicarboxylic acid 2-{[1-(4'-chloro-biphenyl-3-yl)-ethyl]-amide} 5-hydroxyamide;

Thiophene-2,5-dicarboxylic acid 2-hydroxyamide 5-{[1-(2'-methoxy-biphenyl-3-yl)-ethyl]-amide};

Thiophene-2,5-dicarboxylic acid 2-hydroxyamide 5-{[1-(2'-methyl-biphenyl-3-yl)-ethyl]-amide};

Thiophene-2,5-dicarboxylic acid 2-hydroxyamide 5-{[1-(4'-methoxy-biphenyl-3-yl)-ethyl]-amide}; and Thiophene-2,5-dicarboxylic acid 2-{[1-(4'-dimethylamino-biphenyl-3-yl)-ethyl]-amide} 5-hydroxyamide.

13. A compound of claim 1 selected from the group consisting of:

Thiophene-2,5-dicarboxylic acid 2-{[1-(2'-fluoro-biphenyl-3-yl)-ethyl]-amide} 5-hydroxyamide;

Thiophene-2,5-dicarboxylic acid 2-{[1-(4'-fluoro-biphenyl-3-yl)-ethyl]-amide} 5-hydroxyamide;

Thiophene-2,5-dicarboxylic acid 2-{[1-(3'-fluoro-biphenyl-3-yl)-ethyl]-amide} 5-hydroxyamide;

Thiophene-2,5-dicarboxylic acid 2-hydroxyamide 5-{[1-(4'-methyl-biphenyl-3-yl)-ethyl]-amide}; and Thiophene-2,5-dicarboxylic acid 2-{[1-(2'-chloro-biphenyl-3-yl)-ethyl]-amide} 5-hydroxyamide.

14. A compound of claim 1 selected from the group consisting of:

Thiophene-2,5-dicarboxylic acid 2-{[-(3'-chloro-biphenyl-3-yl)-ethyl]-amide} 5-hydroxyamide;

Thiophene-2,5-dicarboxylic acid 2-hydroxyamide 5-{[1-(3'-methyl-biphenyl-3-yl)-ethyl]-amide};

Thiophene-2,5-dicarboxylic acid 2-hydroxyamide 5-{[1-(3'-methoxy-biphenyl-3-yl)-ethyl]-amide};

Thiophene-2,5-dicarboxylic acid 2-hydroxyamide 5-{[1-(4'-methanesulfonyl-biphenyl-3-yl)-ethyl]-amide}; and Thiophene-2,5-dicarboxylic acid 2-hydroxyamide 5-({1-[4-(1H-pyrazol-4-yl)-phenyl]-ethyl}-amide).

15. A compound of claim 1 selected from the group consisting of:

(R)-Thiophene-2,5-dicarboxylic acid 2-hydroxyamide 5-{[1-(4-thiophen-2-yl-phenyl)-ethyl]-amide};

(R)-Thiophene-2,5-dicarboxylic acid 2-hydroxyamide 5-({1-[4-(5-methyl-thiophen-2-yl)-phenyl]-ethyl}-amide);

Thiophene-2,5-dicarboxylic acid 2-hydroxyamide 5-{[1-(3-thiophen-2-yl-phenyl)-ethyl]-amide};

Thiophene-2,5-dicarboxylic acid 2-{[1-(3-benzo[b]thiophen-2-yl-phenyl)-ethyl]-amide}5-hydroxyamide; and Thiophene-2,5-dicarboxylic acid 2-hydroxyamide 5-({1-[3-(5-methyl-thiophen-2-yl)-phenyl]-ethyl}-amide).

16. A compound of claim 1 selected from the group consisting of:

Thiophene-2,5-dicarboxylic acid 2-hydroxyamide 5-({1-[3-(1H-pyrazol-4-yl)-phenyl]-ethyl}-amide);

Thiophene-2,5-dicarboxylic acid 2-({1-[3-(3,5-dimethyl-isoxazol-4-yl)-phenyl]-ethyl}-amide) 5-hydroxyamide;

Thiophene-2,5-dicarboxylic acid 2-hydroxyamide 5-({1-[3-(1H-indol-5-yl)-phenyl]-ethyl}-amide);

Thiophene-2,5-dicarboxylic acid 2-hydroxyamide 5-{[1-(3-pyridin-3-yl-phenyl)-ethyl]-amide}; and Thiophene-2,5-dicarboxylic acid 2-hydroxyamide 5-{[1-(4-imidazol-1-yl-phenyl)-ethyl]-amide}.

17. A compound of claim 1 selected from the group consisting of:

(R)-Thiophene-2,5-dicarboxylic acid 2-hydroxyamide 5-{[1-(4-morpholin-4-yl-phenyl)-ethyl]-amide};

Thiophene-2,5-dicarboxylic acid 2-hydroxyamide 5-{[1-(4-piperidin-1-yl-phenyl)-ethyl]-amide}; and Thiophene-2,5-dicarboxylic acid 2-hydroxyamide 5-({1-[4-(4-methyl-piperazin-1-yl)-phenyl]-ethyl}-amide); acetic acid salt;

Thiophene-2,5-dicarboxylic acid 2-{[1-(4-cyclohexyl-phenyl)-ethyl]-amide} 5-hydroxyamide;

Thiophene-2,5-dicarboxylic acid 2-hydroxyamide 5-({1-[5-(3-trifluoromethyl-phenyl)-isoxazol-3-yl]-ethyl}-amide); and Thiophene-2,5-dicarboxylic acid 2-hydroxyamide 5-({1-[5-(4-trifluoromethyl-phenyl)-isoxazol-3-yl]-ethyl}-amide).

18. A process for the manufacture of the compounds of formula I in claim 1 comprising:

(a) reacting compounds of formula IV:

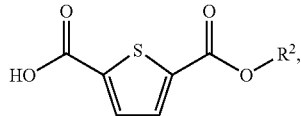

formula IV wherein $R^2$ is an alkyl group;

with racemic, or enantiomerically pure (R)-amines or (S)-amines of formula VII:

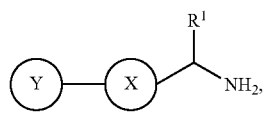

formula VII wherein X, Y and $R^1$ are defined according to claim 9, in the presence of a suitable activating agent, to obtain the compounds of formula VIII:

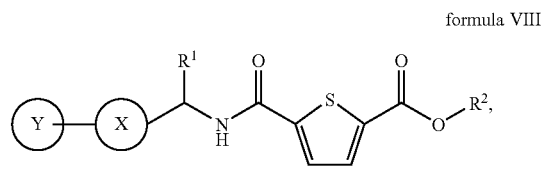

formula VIII wherein X, Y and $R^1$ are defined according to claim 1 and $R^2$ is an alkyl group, (b) treating said compounds of formula VIII with hydroxylamine to obtain the compounds of formula I in claim 1; and (c) optionally transforming said compounds into their pharmaceutically acceptable salts.

19. A pharmaceutical composition comprising a compound of claim 1 and one or more pharmaceutically acceptable excipients, diluents, or adjuvants.

* * * * *